United States Patent
Okui et al.

(10) Patent No.: US 7,371,768 B2
(45) Date of Patent: May 13, 2008

(54) PYRAZOL DERIVATIVES, PEST CONTROL AGENT COMPRISING THE SAME AS ACTIVE INGREDIENT, AND PROCESS FOR PRODUCING THE SAME

(75) Inventors: Shuko Okui, Tokyo (JP); Nobuo Kyomura, Osaka (JP); Toshiki Fukuchi, Osaka (JP); Kazuya Okano, Ibaraki (JP); Liangyou He, Ibaraki (JP); Akiko Miyauchi, Ibaraki (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 345 days.

(21) Appl. No.: 10/355,182

(22) Filed: Jan. 31, 2003

(65) Prior Publication Data

US 2004/0053969 A1    Mar. 18, 2004

Related U.S. Application Data

(63) Continuation-in-part of application No. PCT/JP01/06549, filed on Jul. 30, 2001.

(30) Foreign Application Priority Data

Jul. 31, 2000    (JP)    ............... P2000-230238

(51) Int. Cl.
*A01N 43/56*    (2006.01)

(52) U.S. Cl. .............. 514/357; 546/276.4; 424/405
(58) Field of Classification Search ............... 514/357; 546/275.4
See application file for complete search history.

(56) References Cited

U.S. PATENT DOCUMENTS 6,335,357 B1    1/2002 Okui et al.

FOREIGN PATENT DOCUMENTS

| EP | 0 301 339 | 2/1989 |
|---|---|---|
| EP | 0 511 845 | 11/1992 |
| EP | 0 659 745 A1 | 6/1995 |
| EP | 0 839 809 | 5/1998 |
| WO | WO 98/45274 | 10/1998 |
| WO | WO 01/00614 A1 | 1/2001 |
| WO | WO 02066423 | * 8/2002 |

OTHER PUBLICATIONS

HCAPLUS abstract # 137:59011; Fukuchi -HU 9903081.*

* cited by examiner

*Primary Examiner*—Neil S. Levy
(74) *Attorney, Agent, or Firm*—Oblon, Spivak, McClelland, Maier & Neustadt, P.C.

(57) ABSTRACT

The present invention relates to pest control agent having systemic activity and a high safety along with a wide insecticidal spectrum and excellent insecticidal activity, which are 1-aryl-3-cyano-5-pyridylalkylaminopyrazole derivatives represented by formula (1):

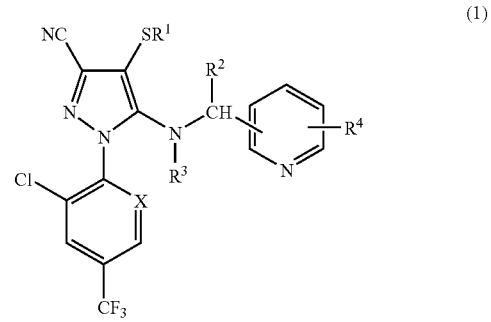

(1)

wherein X represents an N or C-halogen atom; $R^1$ represents a haloalkyl group, excluding a perhaloalkyl group; $R^2$ represents a hydrogen atom or an alkyl group, $R^3$ represents a hydrogen atom, an alkyl group, or an acyl group; and $R^4$ represents a hydrogen atom, a hydroxyl group, an alkyl group, a haloalkyl group, an alkoxy group, a haloalkoxy group, an alkylthio group, an alkylsulfinyl group, an alkylsulfonyl group, a halogen atom, a nitro group, or a cyano group.

1 Claim, No Drawings

PYRAZOL DERIVATIVES, PEST CONTROL AGENT COMPRISING THE SAME AS ACTIVE INGREDIENT, AND PROCESS FOR PRODUCING THE SAME

FIELD OF THE INVENTION

The present invention relates to novel 1-aryl-3-cyano-5-pyridylalkylaminopyrazole derivatives and a pest control agent, particularly an insecticide, comprising the same as an active ingredient.

BACKGROUND OF THE INVENTION

In the agricultural and horticultural field, a wide variety of insecticides as a pest control agent have been hitherto developed and put into practical use for the purpose of controlling various pest insects.

For example, as pyrazole compounds having insecticidal activity, 3-cyano-1-phenylpyrazole derivatives having an amino group which may be substituted at the 5-position are disclosed in JP-A-62-228065, JP-A-63-316771, and JP-A-3-118369, substituted 1-aryl-3-cyano-5-(het)arylmethylideneiminopyrazole derivatives are disclosed in JP-A-5-148240, and substituted 1-aryl-5-(het)arylmethylaminopyrazole derivatives are disclosed in JP-A-64-47768.

However, the compounds disclosed in the above literatures are not necessarily satisfactory in all of insecticidal effects, insecticidal spectrum, safety, and the like, and thus the development of novel compounds overcoming these problems has been desired. As a result, novel 1-aryl-3-cyano-5-heteroarylalkylaminopyrazole derivatives are disclosed as compounds exhibiting a high safety in JP-A-10-338676.

However, the compounds disclosed in JP-A-10-338676 and the like are more excellent in insecticidal activity and have a more reduced toxicity than known compounds but problems that the compounds have insufficient performance in view of systemic activity and that those having a high systemic activity have a relatively insufficient safety have been found. In view of efficient application of an agent for pest control and application for soil treatment especially effective for controlling pest organisms such as fluid-sucking pests, systemic activity is an important factor. Moreover, in recent years, the safety to organisms other than target pest insects and the environment has been increasingly demanded and, hereafter, measures for environmental protection will be strongly taken. Therefore, in order to develop pesticides satisfying more strict regulation, it has been an important problem to find compounds having a higher safety.

SUMMARY OF THE INVENTION

As a result of the intensive studies for solving the above problems, the present inventors have found that a compound having an improved systemic activity and a high safety is obtained by using a pyridyl group as the heteroaryl group attached to the alkylamino group at the 5-position of the pyrazole ring in 1-aryl-3-cyano-5-heteroarylalkylaminopyrazole derivatives and further using a partially halogenated specific alkylthio group as the substituent at the 4-position of the pyrazole ring, and have accomplished the present invention.

Namely, the present invention relates to 1-aryl-3-cyano-5-pyridylalkylaminopyrazole derivatives represented by the following formula (1):

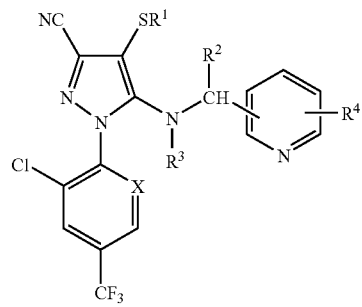

wherein X represents an N or C-halogen atom; $R^1$ represents a haloalkyl group, excluding a perhaloalkyl group; $R^2$ represents a hydrogen atom or an alkyl group; $R^3$ represents a hydrogen atom, an alkyl group, or an acyl group; and $R^4$ represents a hydrogen atom, a hydroxyl group, an alkyl group, a haloalkyl group, an alkoxy group, a haloalkoxy group, an alkylthio group, an alkylsulfinyl group, an alkylsulfonyl group, a halogen atom, a nitro group, or a cyano group, and a pest control agent comprising the derivative as an active ingredient, and a process for producing the compound.

DETAILED DESCRIPTION OF THE INVENTION

The present invention is explained below in detail.

In the present invention, the substituent $R^1$ in the compounds represented by the above formula (1) represents a partially halogenated linear or branched alkyl group such as a fluoromethyl group, a difluoromethyl group, a 2-fluoroethyl group, a 2-chloroethyl group, a 2,2,2-trifluoroethyl group, a 2,2,2-trichloroethyl group, a 3-chloropropyl group, a 3-bromopropyl group, a 3,3,3-trifluoropropyl group, a 2,2,3,3-tetrafluoropropyl group, a 2,2,3,3,3-pentafluoropropyl group, a 2,2-dichloro-3,3,3-trifluoropropyl group, a 2,2-dichloro-3,3,3-trifluoropropyl group, a 3,3,3-trichloropropyl group, a 4-chlorobutyl group, a 4,4,4-trifluorobutyl group, or a 3,3,4,4,4-pentafluorobutyl group. Among these, a haloalkyl group having 1 to 4 carbon atoms is preferable, and a haloalkyl group having 1 to 2 carbon atoms such as a fluoromethyl group, and a difluoromethyl group is particularly preferable.

$R^2$ represents a hydrogen atom; a linear or branched alkyl group such as a methyl group, an ethyl group, an n-propyl group, an isopropyl group, an n-butyl group, an isobutyl group, a sec-butyl group, or a t-butyl group. Among these, a hydrogen atom and an alkyl group having 1 to 4 carbon atoms are preferable, and a hydrogen atom is particularly preferable.

$R^3$ represents a hydrogen atom; a linear or branched alkyl group such as a methyl group, an ethyl group, an n-propyl group, an isopropyl group, an n-butyl group, an isobutyl group, a sec-butyl group, or a t-butyl group; or a linear or branched acyl group such as a methylcarbonyl group, an ethylcarbonyl group, an n-propylcarbonyl group, an isopropylcarbonyl group, an n-butylcarbonyl group, an isobutylcarbonyl group, a sec-butylcarbonyl group, or a t-butylcarbonyl group. As the above alkyl group and acyl group, those having 1 to 4 carbon atoms are preferable. As $R^3$, a hydrogen atom is particularly preferable.

R⁴ represents a hydrogen atom; a hydroxyl group; a linear or branched alkyl group such as a methyl group, an ethyl group, an n-propyl group, an isopropyl group, an n-butyl group, an isobutyl group, a sec-butyl group, or a t-butyl group; a linear or branched haloalkyl group such as a difluoromethyl group, a trifluoromethyl group, a 2-fluoroethyl group, a 2-chloroethyl group, a 2,2,2-trifluoroethyl group, a 2,2,2-trichloroethyl group, a 3-chloropropyl group, a 3-bromopropyl group, a 3,3,3-trifluoropropyl group, a 2,2,3,3-tetrafluoropropyl group, a 2,2,3,3,3-pentafluoropropyl group, a 2,2-dichloro-3,3,3-trifluoropropyl group, a 2,2-dichloro-3,3,3-trifluoropropyl group, a 1,3-difluoro-2-propyl group, a 1,1,1,3,3,3-hexafluoro-2-propyl group, a 3,3,3-trichloropropyl group, a 4-chlorobutyl group, a 4,4,4-trifluorobutyl group, or a 3,3,4,4,4-pentafluorobutyl group; a linear or branched alkoxy group such as a methoxy group, an ethoxy group, an n-propoxy group, an isopropoxy group, an n-butoxy group, isobutoxy group, a sec-butoxy group, or a t-butoxy group; a linear or branched haloalkoxy group such as a difluoromethoxy group, a trifluoromethoxy group, a 2-fluoroethoxy group, a 2-chloroethoxy group, a 2,2,2-trifluoroethoxy group, a 2,2,2-trichloroethoxy group, a 3-chloropropoxy group, a 3-bromopropoxy group, a 3,3,3-trifluoropropoxy group, a 2,2,3,3-tetrafluoropropoxy group, a 2,2,3,3,3-pentafluoropropoxy group, a 2,2-dichloro-3,3,3-trifluoropropoxy group, a 2,2-dichloro-3,3,3-trifluoropropoxy group, a 1,3-difluoro-2-propoxy group, a 1,1,1,3,3,3-hexafluoro-2-propoxy group, a 3,3,3-trichloropropoxy group, a 4-chlorobutoxy group, a 4,4,4-trifluorobutoxy group, or a 3,3,4,4,4-pentafluorobutoxy group; a linear or branched alkylthio group such as a methylthio group, an ethylthio group, an n-propylthio group, an isopropylthio group, an n-butylthio group, an isobutylthio group, a sec-butylthio group, or a t-butylthio group; a linear or branched alkylsulfinyl group such as a methylsulfinyl group, an ethylsulfinyl group, an n-propylsulfinyl group, an isopropylsulfinyl group, an n-butylsulfinyl group, an isobutylsulfinyl group, a sec-butylsulfinyl group, or a t-butylsulfinyl group; a linear or branched alkylsulfonyl group such as a methylsulfonyl group, an ethylsulfonyl group, an n-propylsulfonyl group, an isopropylsulfonyl group, an n-butylsulfonyl group, isobutylsulfonyl group, a sec-butylsulfonyl group, or a t-butylsulfonyl group; a halogen atom such as a chlorine atom, a fluorine atom, or a bromine atom; a nitro group; or a cyano group. Among these, as the above alkyl group, haloalkyl group, alkoxy group, haloalkoxy group, alkylthio group, alkylsulfinyl group, and alkylsulfonyl group, those having 1 to 4 carbon atoms are preferable. Particularly, as R⁴, a hydrogen atom and an alkyl group are preferable, and a hydrogen atom is most preferable.

In the compounds of the above formula (1), the compounds derived from the combinations of preferable substituent in each of R¹ to R⁴ are more preferable.

Examples of preferable combinations of the above substituents include compounds wherein R¹ is a partially halogenated alkyl group having 1 to 2 carbon atoms and R², R³ and R⁴ are hydrogen atoms. Among these, those wherein R¹ is a fluoromethyl group or difluoromethyl group are preferable because they exhibit a high insecticidal activity (i.e., a sufficient insecticidal effect is obtained even at a low concentration of the compounds) when they are used as active ingredients in pest control agents, particularly insecticides. The most preferable compound is 1-(2,6-dichloro-4-trifluoromethylphenyl)-4-difluoromethylthio-5-(pyridin-2-ylmethylamino)pyrazole-3-carbonitrile as shown below.

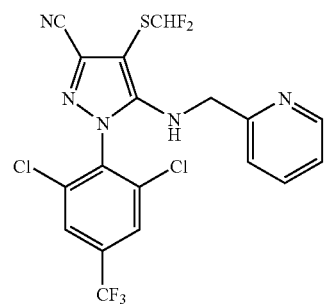

As the process for producing the compounds of the present invention represented by the above formula (1), the process for the production described in JP-A-10-338676 can be used. Additionally, the processes shown in the following Reaction Schemes 1 to 4 can be exemplified as preferable other methods.

Reaction Scheme 1

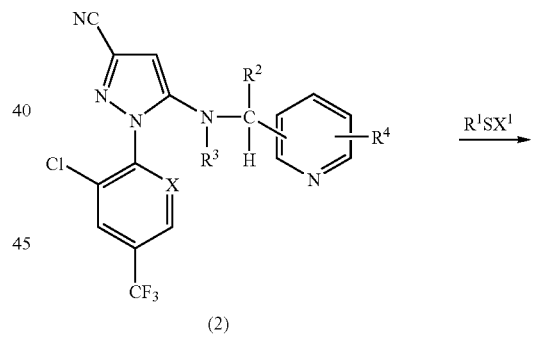

(2)

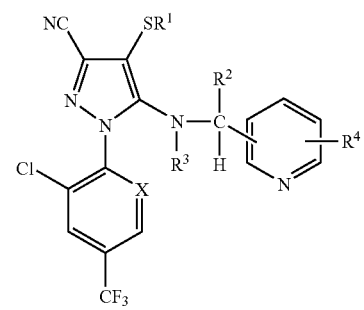

Reaction Scheme 2

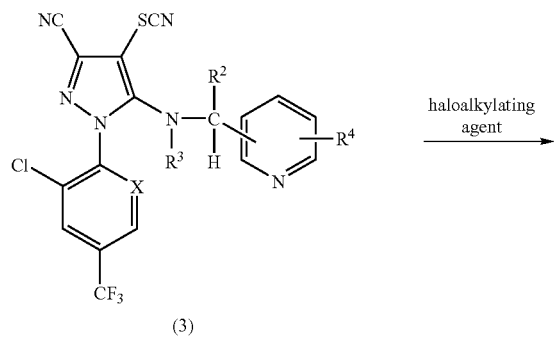

Reaction Scheme 4

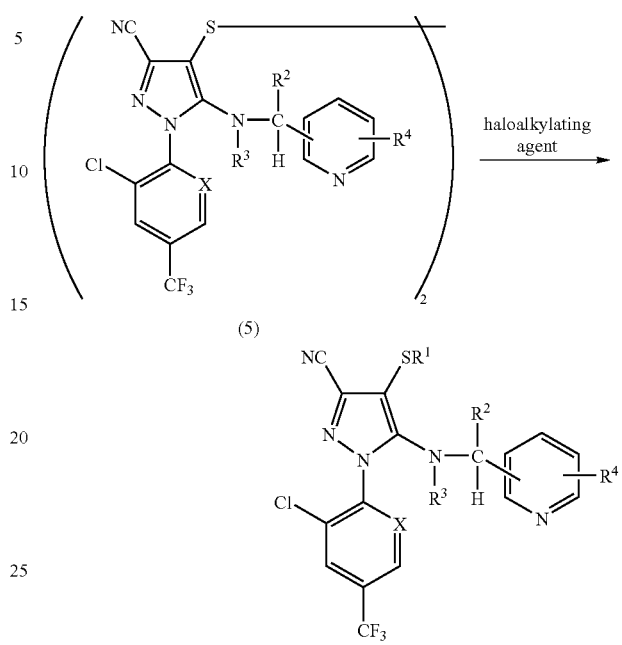

Reaction Scheme 3

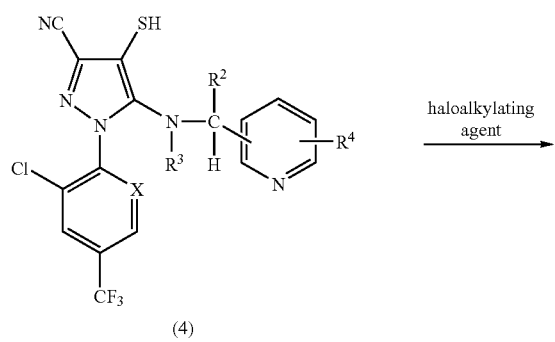

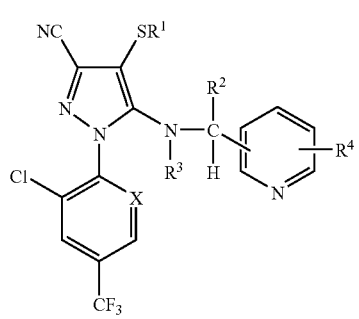

(wherein $R^1$, $R^2$, $R^3$, $R^4$ and X have the same meanings as described above)

Reaction Scheme 1 shows a process for producing a pyrazole derivative of formula (1), which comprises treating a pyrazole derivative of formula (2) with $R^1SX^1$ wherein $R^1$ has the same meaning as in formula (1) and $X^1$ represents a chlorine atom, a bromine atom, an alkylsulfonyl group, or an arylsulfonyl group. $X^1$ is preferably a chlorine atom. Specific examples of $R^1SX^1$ include difluoromethylsulfenyl chloride ($CHF_2SCl$) and the compound can be produced by the method described in *J. Org. Chem.*, Vol. 44, No. 10, 1708 (1979).

In the reaction, $R^1SX^1$ is used in an amount of 0.5 to 10.0 molar equivalents, preferably 0.8 to 5 molar equivalents, to the compound represented by formula (2) and the reaction is carried out at 0° C. to 150° C., preferably 0° C. to 100° C., generally for 1 to 24 hours, preferably 1 to 4 hours, which may vary depending on a reaction scale.

The solvent for use in the reaction includes an aromatic hydrocarbon such as benzene, toluene, and xylene; a ketone such as acetone and methyl ethyl ketone; a halogenated hydrocarbon such as chloroform and methylene chloride; an ether solvent such as ether, diisopropyl ether, and tetrahydrofuran; an aprotic polar solvent such as N,N-dimethylformamide (DMF) and dimethyl sulfoxide; and the like. Among these, toluene and dichloromethane are preferable.

The reaction is carried out preferably in the presence of a base, and an amine such as pyridine or triethylamine is used as the base.

Reaction Scheme 2 shows a process for producing a pyrazole derivative of formula (1), which comprises treating a pyrazole derivative of formula (3) with a haloalkylating agent.

Examples of the haloalkylating agent for use in the reaction include fluoromethyl bromide, difluoromethyl chloride, trimethylsilyldifluoromethane, and the like.

The solvent for use in the reaction includes an ether solvent such as tetrahydrofuran, diethyl ether, and dimethoxy ethane; a hydrocarbon solvent such as toluene and hexane; a halogenated hydrocarbon solvent such as dichloromethane and chloroform; and the like. Among these, tetrahydrofuran is preferable.

In the reaction, the haloalkylating agent is used in an amount of 0.5 to 10.0 molar equivalents, preferably 0.8 to 5 molar equivalents to the compound represented by formula (3) and the reaction is carried out at −20° C. to 120° C., preferably 0° C. to room temperature, generally for 1 to 24 hours, preferably 1 to 4 hours, which may vary depending on a reaction scale.

Reaction Scheme 3 shows a process for producing a pyrazole derivative of formula (1), which comprises treating a pyrazole derivative of formula (4) with a haloalkylating agent.

Examples of the haloalkylating agent include a haloalkylating agent having a halomethyl group. The haloalkylating agent having a halomethyl group is preferably a compound having a difluoromethyl group, and more preferably a compound known as a difluorocarbene precursor. Examples of the difluorocarbene precursor include compounds described in *Organofluorine Compounds*, p 107-111, written by Hiyama, published by Springer, and specific examples include difluoromethyl chloride, chlorodifluoroacetic acid, chlorodifluoroacetic acid metal salts, chlorodifluoroacetic acid esters, and the like.

The solvent for use in the reaction includes an aprotic polar solvent such as N,N-dimethylformamide (DMF) and dimethyl sulfoxide (DMSO); an alcohol solvent such as methanol, ethanol, and isopropanol; a hydrocarbon solvent such as toluene and hexane; a halogenated hydrocarbon solvent such as dichloromethane and chloroform; a basic solvent such as triethylamine and liquid ammonia; and the like. Among these, a polar solvent such as DMF and an alcohol solvent such as ethanol and isopropanol are preferable.

The reaction is carried out at −20° C. to 200° C., preferably 0° C. to 150° C. for 1 to 24 hours, preferably 1 to 4 hours.

Also, the reaction may be carried out as a two-layer system. In that case, the solvent includes a two-layer system of a polar solvent such as dioxane or a hydrocarbon solvent such as toluene or xylene and a concentrated aqueous sodium hydroxide solution. The reaction is carried out in the presence of a phase transfer catalyst such as tetrabutylammonium bromide at a reaction temperature of −20° C. to 120° C., preferably 0° C. to room temperature, generally for 1 to 24 hours, preferably 1 to 4 hours, which may vary depending on a reaction scale.

Reaction Scheme 4 shows a process for producing a pyrazole derivative of formula (1), which comprises treating a pyrazole derivative of formula (5) with a haloalkylating agent.

In the reaction, the reaction is carried out in the presence of a reducing agent, if necessary.

Examples of the reducing agent include hydrides such as sodium borohydride, zinc borohydride, and lithium aluminum hydride; metal zinc; hydrazine; and the like. The amount to be used is in the range of 1 to 20 molar times, preferably 1 to 5 molar times, to the substrate.

The other reagents and conditions to be used are the same as the explanations with regard to the above formula (3).

In this connection, the compound of the above formula (3), (4) or (5) can be produced by known methods using the compound of formula (2) as a starting material.

In the case of 1-(2,6-dichloro-4-trifluoromethylphenyl)-4-difluoromethylthio-5-(pyridin-2-ylmethylamino)pyrazole-3-carbonitrile which is the most preferable in the compounds of the present invention, the route shown in Reaction Scheme 1' and Reaction Scheme 4' are mentioned exemplified as particularly preferable processes for the production.

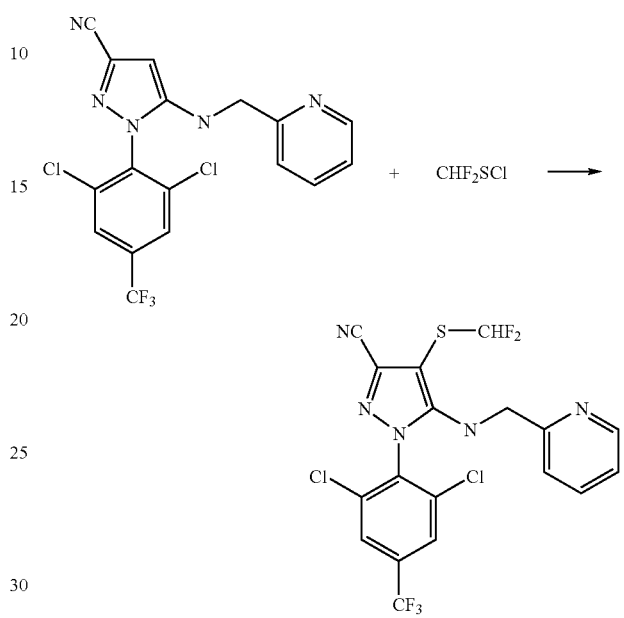

Reaction Scheme 1'

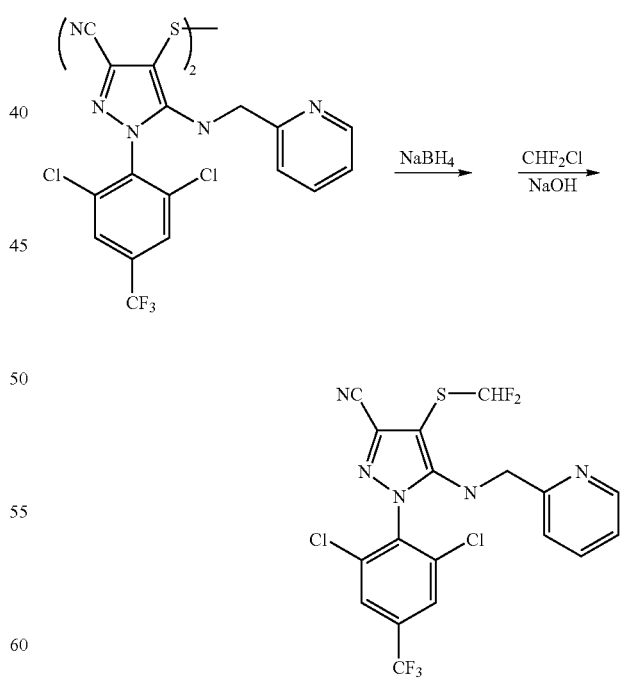

Reaction Scheme 4'

Next, the process for producing the pyrazole derivative represented by formula (2) is described. Two kinds of processes are exemplified as the processes for producing the pyrazole derivative represented by formula (2).

1) A process for converting a side chain of a pyrazole derivative
2) A process for obtaining an objective compound through synthesizing the pyrazole skeleton In the process for converting a side chain of a pyrazole derivative in 1), a process for producing an amine which is commonly known (for example, the process described in *Organic Functional Group Preparations I*, p 377, chapter 13 (Amines), Academic Press, 1983) is applicable. Specifically, the pyrazole derivative represented by formula (2) can be produced using the compound represented by formula (6), (7), or (8) as a starting material by the processes shown in Reaction Schemes 5 to 8.

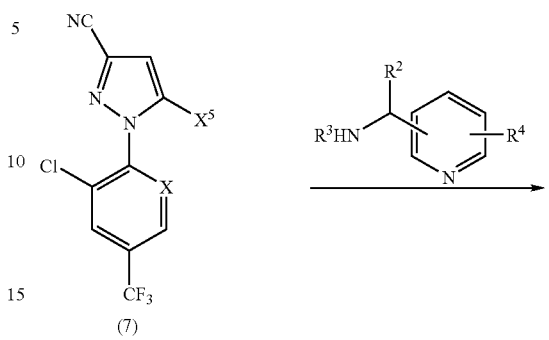

Reaction Scheme 6

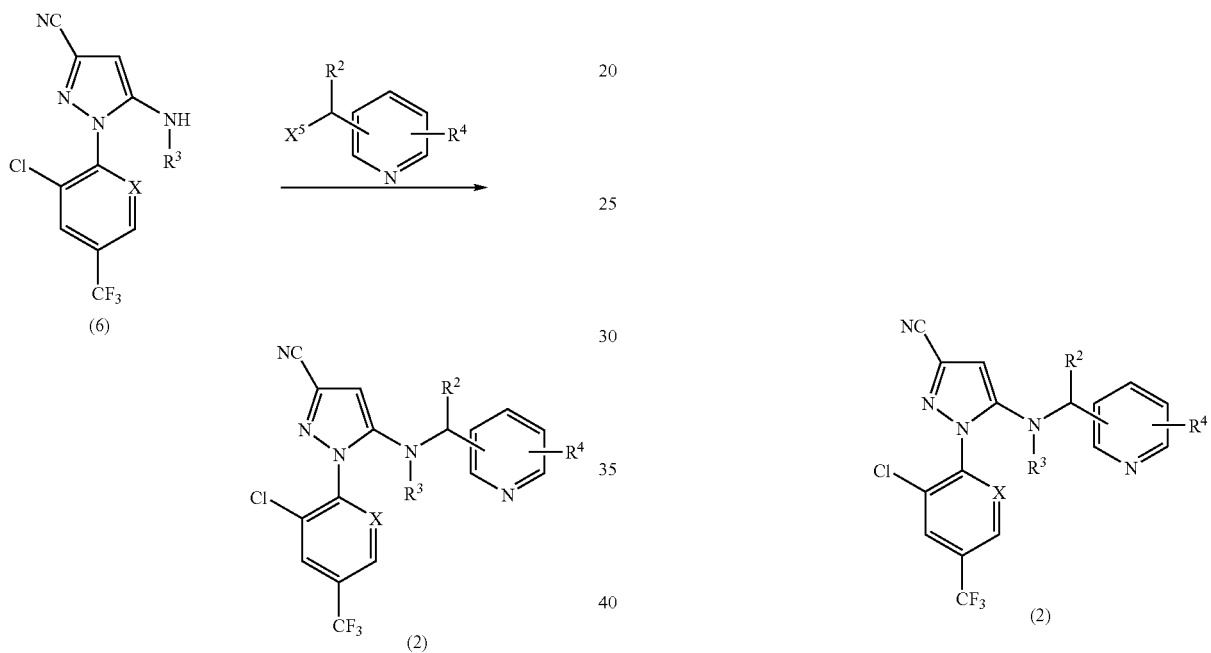

Reaction Scheme 5

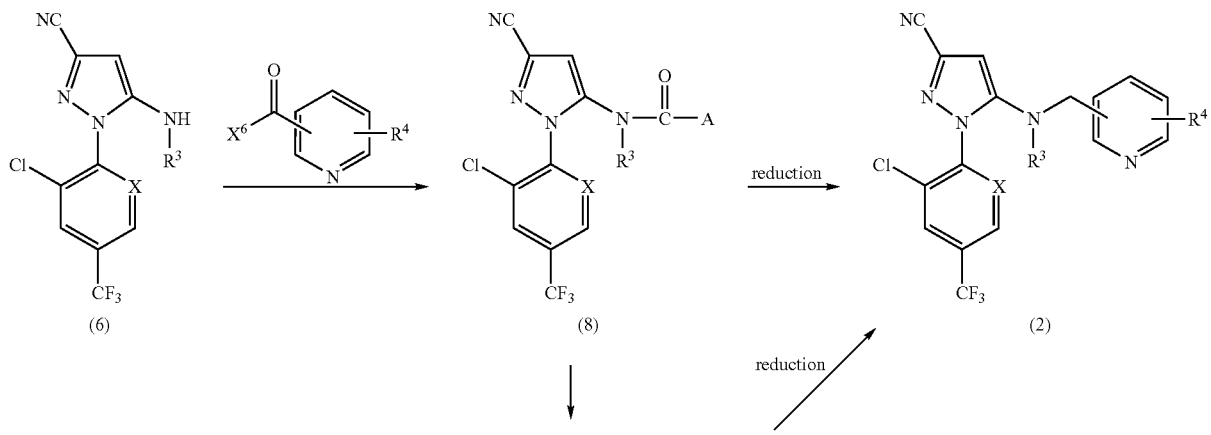

Reaction Scheme 7

-continued

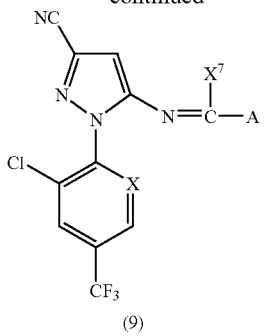

(9)

Reaction Scheme 8

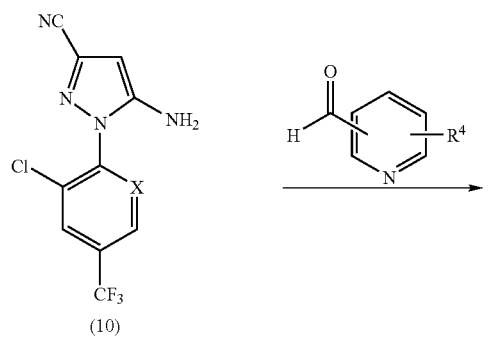

(10)

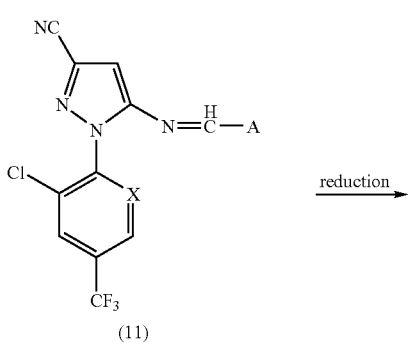

(11)

↓ reduction

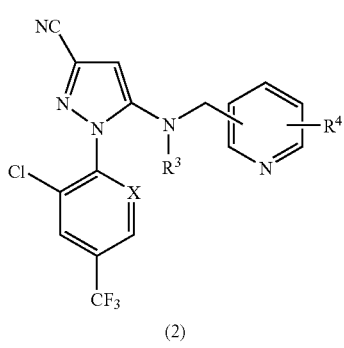

(2)

(wherein X, $R^2$, $R^3$, and $R^4$ have the same meanings as in formula (1); $X^5$ represents a leaving group such as a halogen atom or a hydroxyl group; $X^6$ represents a halogen atom, a hydroxyl group, or an alkoxy group; $X^7$ represents a halogen atom; and A represents an $R^4$-pyridyl group)

In the condensation reactions in the above Reaction Schemes, each of them can be carried out in accordance with a known method.

Moreover, as the reducing agent for use in the reduction, a reagent for use in the usual reduction of an imine, amide or haloimidate can be utilized, and hydrogen or a hydrogen-donating substance is used. When hydrogen is used, a catalyst such as palladium or platinum is usually used. Examples of the hydrogen-donating substance include organic hydrogen-donating substances such as formic acid and isopropanol; inorganic hydrogen-donating substances such as hydrazine; metal hydrides; and the like. The metal hydrides include boran-THF complex, sodium borohydride, sodium cyanoborohydride, lithium borohydride, lithium aluminum hydride, and the like. In the case of Reaction Scheme 8, so-called reductive amination wherein a) formation of an imine compound (10) and b) formation of a pyrazole derivative (2) by reduction are carried out in the same step is also effective.

The solvent for use in the reaction includes a polar solvent, for example, an ether such as diethyl ether, dioxane, and tetrahydrofuran; alcohol such as methanol, ethanol, and propanol; and the like.

The reaction is carried out at a temperature of −20° C. to 120° C., preferably 0° C. to room temperature, for 1 to 24 hours, preferably 1 to 4 hours.

The chlorinating agent for use in the haloimidation includes phosphorus pentachloride, phosphorus oxy chloride, thionyl chloride, and the like.

The solvent for use in the reaction includes a nonpolar solvent such as benzene, toluene, and xylene; a halogenated solvent such as carbon tetrachloride, chloroform, and dichloromethane; an ether solvent such as dimethoxyethane and tetrahydrofuran; and the like.

The reaction is carried out at a temperature of 0° C. to 200° C., preferably room temperature to 150° C., for 1 to 24 hours, preferably 1 to 4 hours.

As the process for obtaining an objective compound through synthesizing the pyrazole skeleton in 2), various general processes are described in JP-A-10-338676, but the process represented by Reaction Scheme 9 is exemplified as a preferable one.

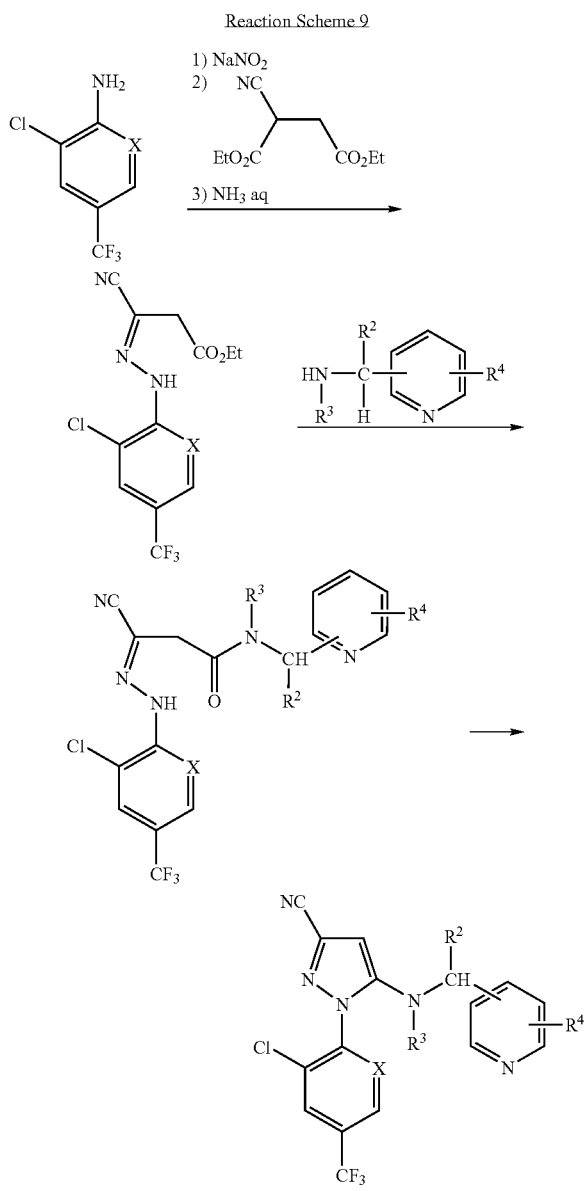

The pest control agent comprising the compound of the present invention as an active ingredient has an effect of controlling pests such as pest insects and mites, and is effective for repelling, expelling, and controlling pests in wide range of cases, for example, at agriculture, forestry, stock raising, fisheries, and preservation of the products of these industries, and public health.

In particular, the compound of the present invention exhibits excellent effects as insecticides and acaricides for use at repelling, expelling, and controlling pests in agriculture, forestry, and the like, specifically pests damaging agricultural crops at their raising, harvested crops, trees, plants for appreciation, and the like, and pests in cases for the public health.

Specific application cases, target pests, application methods, and the like are described below, but the present invention is not limited thereto. Furthermore, target pests are not limited to those specifically described, and the pests include their imagoes, larvae, eggs, and the like.

(A) Cases Such as Agriculture and Forestry

The pest control agent comprising the compound of the present invention as an active ingredient is effective for repelling and controlling pests such as arthropods, mollusks, nematoda, various fungi, and the like, which damage agricultural crops, such as food crops (e.g., rice plant, oats, maize, potato, sweet potato, beans), vegetables (e.g., brassicaceous crops, cucurbitaceous fruits, eggplant, tomato, onions), fruit trees (e.g., citrus fruits, apple, grapes, peach), industrial crops (e.g., tobacco, tea, sugar beet, sugar cane, cotton, olive), crops for pasture and feed (e.g., solgums, grass pastures, leguminous pastures), plants for appreciation (e.g., herbage, flowers and ornamental plants, garden trees) at the raising of these crops. Furthermore, the compound of the present invention is also effective for repelling and controlling pests at the storage of harvest products from the above crops, for example, food grains, fruits, nuts, spices, and tobacco, and products resulting from subjecting them to a treatment such as drying or pulverization. Moreover, the compound is also effective for protecting standing trees, fallen trees, processed timber, stored woods from the damage by pests such as termites or beetles.

Specific examples of pests belonging to Arthropoda, Mollusca, and Nematoda are described below. Examples of Arthropoda Insecta are described below.

Examples of Lepidoptera include Noctuidae such as *Leucania unipuncta, Heliothis assulata, Barathra brassicae*, and *Plusia peponis*; Putellidae such as *Plutella xylostella*; Tortricidae such as *Homona magnanima* and *Grapholita molesta*; Psychidae such as *Canephora asiatica*; Lyonetiidae such as *Lyonetia clerkella*; Lithocolletidae such as *Lithocolletis ringoniella*; Acrolepiidae such as *Acrolepia alliella*; Aegeriidae such as *Aegeria molybdoceps*; Heliodinidae such as *Kakivoria flavofasciata*; Gelechiidae such as *Pectinophora gossypiella*; Carposinidae such as *Carposina nipponensis*; Heterogeneidae such as *Cnidocampa flavescens*; Pyralidae such as *Cnaphalocrocis medinalis, Chilo suppressalis*, and *Natarcha derogate*; Hesperiidae such as *Parnara quttata*; Papilionidae such as *Papilio machaon*; Pieridae such as *Pieris rapae*; Lycaenidae such as *Lampides boeticus*; Geometridae such as *Ascotis selenaria cretacea*; Sphingidae such as *Herse convolvuli*; Notodontidae such as *Phalera flavescens*; Lymantriidae such as *Euproctis subflava*; Arctiidae such as *Hyphantria cunea*; and the like.

Examples of Coleoptera include Scarabaeidae such as *Anomala cuprea, Oxycetonia jucunda*, and *Popillia japonica*; Buprestidae such as *Agrilus auriventris*; Elateridae such as *Melanotus legatus*; Coccinellidae such as *Epilachna vigintioctopunctata*; Cerambycidae such as *Anoplophora malasiaca* and *Xylotrechus pyrrhoderus*; Chrysomelidae such as *Aulacophora femoralis, Phyllotreta striolata*, and *Donacia provostii*; Attelabidae such as *Phynchites heros*; Brenthidae such as *Cylas formicarius*; Curculionidae such as *Curculio sikkimensis* and *Echinocnemus squameus*; and the like.

Examples of Hemiptera include Pentatomidae such as *Plautia stali* and *Halyomorpha halys*; Urostylidae such as *Urochela luteovaria*; Coreidae such as *Cletus punctiger*; Alydidae such as *Leptocorisa chinensis*; Pyrrhocoridae such as *Dysdercus cingulatus*; Tingidae such as *Stephanitis nashi*; Miridae such as *Deraeocoris amplus*; Cicadidae such as *Platypleura kaempferi*; Aphrophoridae such as *Dophoara vitis*; Tettigellidae such as *Oniella leucocephala*; Cicadellidae such as *Arboridia apicalis* and *Empoasca onukii*; Deltocephalidae such as *Nephotettix cincticeps*; Delphacidae such as *Laodelphax striatellus* and *Nilaparvata lugens*; Flatidae such as *Geisha distinctissima*; Psylloidae such as

*Psylla pyrisuga*; Aleyrodidae such as *Trialeurodes vaporariorum* and *Bemisia argentifolii*; Phylloxeridae such as *Moritziella costaneivora*; Pemphigidae such as *Eriosoma lanigera*; Aphididae such as *Aphis gossypii*, *Myzus persicae*, and *Rhopalosiphum rufiabdominalis*; Margarodidae such as *Icerya purchasi*; Pseudococcidae such as *Planococcus citri*; Coccidae such as *Ceroplastes rubens*; Diaspididae such as *Quadraspidiotus perniciosus* and *Pseudaulacaspis pentagana*; and the like.

Examples of Thysanoptera include Thripidae such as *Frankliniella occidentalis, Scirtothrips dorsalis*, and *Thrips palmi*; Phlaeothripidae such as *Ponticulothrips diospyrosi* and *Haplothrips aculeatus*; and the like.

Examples of Hymenoptera include Tenthredinidae such as *Athalia japonicav*; Argidae such as *Arge mali*; Cynipidae such as *Dryocosmus kuriphilus*; Megachilidae such as *Megachile nipponica*; and the like.

Examples of Dioptera include Cecidomyiidae such as *Asphondylia* sp.; Tephiridae such as *Zeugodacus cucurbitae*; Ephydridae such as *Hydrellia griseola*; Drosophilidae such as *Drosophila suzukii*; Agromyzidae such as *Chromatomyia horticola* and *Liriomyza trifolii*; Anthomyiidae such as *Hylemya antiqua*; and the like.

Examples of Orthoptera include Tettigoniidae such as *Homorocoryphus nitidulus*; Gryllidae such as *Calyptotrypes hihinonis*; Gryllotalpidae such as *Gryllotalpa afrcana*; Acrididae such as *Oxya japonica*; and the like.

Examples of Collembola include Sminthuridae such as *Sminthurus viridis*; Onychiuridae such as *Onychiurus matsumotoi*; and the like.

Examples of Isoptera include Termitidae such as *Odontotermes formosanus*, and the like. Examples of Dermaptera include Labiduridae such as *Labidura riparia*, and the like.

Examples of Arthropoda Crustacea and Arachnida are described below.

Examples of Crustacea Isopoda include Armadillidiidae such as *Armadillidium vulgare*, and the like.

Examples of Arachnida Acarina include Tarsonemidae such as *Hemitarsonemus latus* and *Tarsonemus pallidus*; Eupodidae such as *Penthaleus* major; Tenuipalpidae such as *Brevipalpus lewisi*; Tetranychidae such as *Tetranychus urticae, Tetranychus kanzawai, Panonychus citri*, and *Panonychus ulmi*; Eriophyidae such as *Aculus pelekassi, Aculus schlechtendali*, and *Eriophyyes chibaensis*; Acaridae such as *Tyrophagus putrescentiae*; and the like.

As Mollusca Gastropoda, examples of Gastropoda Mesogastropoda include *Pomacea canaliculata*, and the like. Examples of Stylommatophora include *Achatina fulica, Incilaria bilineata, Milax gagates, Limax maximus, Acusta despecta*, and the like.

Examples of Nematoda Secernentea and Adenophorea are described below.

Examples of Secernentea Tylenchida include Anguinidae such as *Ditylenchus destructor*; Tylenchorhynchidae such as *Tylenchorhynchus claytoni*; Pratylenchidae such as *Pratylenchus penetrans* and *Pratylenchus coffeae*; Hoplolaimidae such as *Helicotylenchus dihystera*; Heteroderidae such as *Heterodera rostochiensis*; Meloidogynidae such as *Meloidogyne incognita*; Criconematidae such as *Criconemoides*; Nothotylenchidae such as *Nothotylencus acris*; Aphelenchoidae such as *Aphelenchoides fragariae*; and the like.

Examples of Adenophorea Dorylaimida include Longidoridae such as *Xiphinema americanum*; Trichdoridae such as *Paratrichodorus porosus*; and the like.

Furthermore, the compound of the present invention is also effective for repelling, controlling, expelling pests damaging or affecting natural forest, artificial forest, trees in urban green districts, and the like. In such a case, specific pests are described below. Examples of Arthropoda Insecta and Arachnida are described below.

Examples of Lepidoptera include Lymantriidae such as *Dasychira argentata* and *Lymantria disper japonica*; Lasiocampidae such as *Dendrolimus spectabilis* and *Malacosoma neustria*; Pyralidae such as *Dioryctria abietella*; Noctuidae such as *Agrotis fucosa*; Tortricidae such as *Ptycholomoides aeriferana, Laspeyresia kurokoi*, and *Cydia cryptomeriae*; Arctiidae such as *Hyphantria cunea*; Nepticulidae such as *Stigmella malella*; Heterogeneidae such as *Parasa consocia*; and the like.

Examples of Coleoptera include Scarabaeidae such as *Anomala rufocuprea* and *Heptophylla picea*; Buprestidae such as *Agrilus spinipennis*; Cerambycidae such as *Monochamus alternatus*; Chrysomelidae such as *Lypesthes itoi*; Curculionidae such as *Scepticus griseus* and *Shirahoshizo coniferae*; Rhynchophoridae such as *Sipalinus gigas*; Scolytidae such as *Tomicus piniperda* and *Indocryphalus aceris*; Bostrychidae such as *Rhizopertha dominica*; and the like.

Examples of Hemiptera include Aphididae such as *Cinara todocola*; Adelgidae such as *Adelges japonicus*; Diaspidiae such as *Aspidiotus cryptomeriae*; Coccidae such as *Ceroplastes pseudoceriferus*; and the like.

Examples of Hymenoptera include Tenthredinidae such as *Pristiphora erichsoni*; Diprionidae such as *Nesodiprion japonica*; Cynipidae such as *Dryocosmus kuriphilus*; and the like.

Examples of Dioptera include Tipulidae such as *Tipula aino*; Anthomyiidae such as *Hylemya platura*; Cecidomyiidae such as *Contarinia inouyei* and *Contarinia matsusintome*; and the like.

Examples of Arachnida Acaria include *Oligonychus hondoensis, Oligonychus unuguis*, and the like.

Examples of Nematoda Secernentea Tylenchida include Paracytaphelenchidae such as *Bursaphelenchus xylophilus*, and the like.

The pest control agent comprising the compound of the present invention as an active ingredient can be employed as any preparation or any usable form prepared by formulation effective on the above agricultural or forestry cases, alone or in combination with or as a mixed preparation with other active compounds such as an insecticide, acaricide, nematicide, fungicide, synergist, plant regulator, herbicide, and toxic feed. Specific examples of the above other active compounds are described below, which are not limited thereto.

As active compounds such as insecticides or acaricides, examples of organophosphorus agents include dichlorvos, fenitorothion, malathion, naled, chlorpyrifos, diazinon, tetrachorvinphos, fenthion, isoxathion, methidathion, salithion, acephate, demeton-S-methyl, disulfoton, monocrotophos, azinephos-methyl, parathion, phosalone, pyrimiphos-methyl, and prothiofos. Examples of carbamate agents include methorcarb, fenobcarb, propoxur, carbaryl, ethiofencarb, pyrimicarb, bendiocarb, carbosulfan, carbofuran, methomyl, thiodicarb, and the like. Examples of organochlorine agents include lindane, DDT, endosulfan, aldrin, chlordene, and the like. Examples of pyrethroid agents include permethrin, cypermethrin, deltamethrin, cyhalothrin, cyfluthrin, acrinathrin, fenvalerate, ethofenprox, silafluofen, fluvalinate, flucythrinate, bifenthrin, allethrin, phenothrin, fenpropathrin, cyphenothrin, furamethrin, resmethrin, transfurthrin, prallethrin, flufeneprox, halfenprox, imiprothrin, and the like. Examples of neonicotinoid agents include imidacloprid, nitenpyram, acetamiprid, dinotefuran, thiamethoxam, thiacloprid, clothianidin, and the like.

Examples of insect growth regulators such as phenylbenzoylurea include diflubenzuron, chlorfluazuron, triflumuron, flufenoxuron, hexaflumuron, lufenuron, teflubenzuron, buprofezin, tebufenozide, chromafenozide, methoxyfenozide, cyromazine, and the like.

Examples of juvenile hormone agents include pyriproxyfen, fenoxycarb, methoprene, hydroprene, and the like.

Examples of insecticidal substances produced by microorganisms include abamectin, milbemectin, nikkomycin, emamectin benzoate, ivermectin, spinosad, and the like.

Examples of other insecticides include cartap, bensultap, chlorfenapyr, diafenthiuron, nicotine sulfate, metaldehyde, fipronil, pymetrozine, indoxacarb, tolfenpyrad, pyridalyl, and the like.

Examples of acaricides includes dicofol, phenisobromolate, benzomate, tetradifon, polynactins, amitraz, propargite, fenbutatin oxide, tricyclohexyltin hydroxide, tebufenpyrad, pyridaben, fenpyroximate, pyrimidifen, fenazaquin, clofentezine, hexathiazox, acequinocyl, chinomethionat, fenothiocarb, ethoxazole, bifenazate, fluacrypyrim, and the like.

Examples of active compounds of nematicides include methyl isocyanate, fosthiazate, oxamyl, mesulfenfos, cadusafos, and the like.

Examples of toxic feeds include monofluoroacetic acid, warfarin, coumatetralyl, diphacinone, and the like.

Examples of active compounds of fungicides include inorganic coppers, organic coppers, sulfur, maneb, thiram, thiadiazine, captan, chlorothalonil, iprobenfos, thiophanate methyl, benomyl, thiabendazole, iprodione, procymidone, pencycuron, metalaxyl, sandofan, byleton, triflumizole, fenarimol, triforine, dithianon, triazine, fluazinam, probenasole, diethofencarb, isoprothiolane, pyroquilon, iminoctadine acetate, echlomezol, dazomet, kresoxime methyl, carpropamid, diclocymet, tricyclozole, probenazole, ipconazole, azoxystrobin, metominostrobin, acibenzolar-S-methyl, fenoxanil, the compound represented by Code No. NNF-9850 (Nihon Nohyaku Co., Ltd.), the compound represented by Code No. BJL-003 (BASF), the compound represented by Code No. DF-391 (Dainippon Ink & Chemicals, Incorporated), and the like.

Examples of active compounds of synergists include bis(2,3,3,3-tetrachloropropyl) ether, N-(2-ethylhexyl)bicyclo[2.1.1]hept-5-ene-2,3-dicarboxyimide, α-[2-(2-butoxyethoxy)ethoxy]-4,5-methylenedioxy-2-propyltoluene, and the like.

Examples of active compounds of herbicides include bialaphos, sethoxydim, trifluralin, mefenacet, and the like. Examples of active compounds of plant regulators include indoleacetic acid, ethephon, 4-CPA, and the like.

Examples of active compounds of repellents include carane-3,4-diol, N,N-diethyl-m-triamide (Deet), limonene, linalool, citronellal, menthone, hinokitiol, menthol, geraniol, eucalyptol, and the like.

The pest control agent of the present invention may be employed in any forms, and the compound of formula (1) is formulated together with auxiliaries for pesticides to produce preparations, e.g., wettable powders, wettable granules, aqueous solutions, emulsions, liquids, flowable agents including suspensions in water and emulsions in water, capsules, dusts, granules, and aerosols, which are then used. Any amount of the active ingredient compound such as the compound of the present invention may be contained in the preparations but the content is usually selected from the range of from 0.001 to 99.5% by weight as total amount of the active ingredients, being appropriately decided in accordance with various conditions such as the form of the preparation and the method of application. For example, it is preferable to produce the preparations so that the content of the active ingredients ranges about 0.01 to 90% by weight, preferably 1 to 50% by weight, in wettable powders, wettable granules, aqueous solutions, emulsions, liquids, flowable agents, capsules, and the like; about 0.1 to 50% by weight, preferably 1 to 10% by weight, in dusts and granules; or about 0.001 to 20% by weight, preferably 0.01 to 2% by weight, in aerosols and the like.

The auxiliaries for pesticides are used for the purposes of improvement of the repelling effect, controlling effect, and expelling effect against pests, improvement of stabilization and dispersibility, and the like. Examples include carriers (diluents), spreaders, emulsifiers, wetting agents, dispersants, and disintegrators. Liquid carriers include water; aromatic hydrocarbons such as toluene and xylene; alcohols such as methanol, butanol and glycol; ketones such as acetone; amides such as dimethylformamide; sulfoxides such as dimethyl sulfoxide; methylnaphthalene; cyclohexane; animal or vegetable oils; fatty acids; and the like. Solid carriers include clay, kaolin, talc, diatomaceous earth, silica, calcium carbonate, montmorillonite, bentonite, feldspar, quartz, alumina, sawdust, nitrocellulose, starch, gum arabic, and the like. Usual surfactants can be used as emulsifiers or dispersants. For example, anionic, cationic, nonionic or amphoteric surfactants, such as sodium higher alcohol sulfates, stearyltrimethylammonium chloride, polyoxyethylene alkylphenyl ethers, and lauryl betaine, are useful. Furthermore, spreaders such as polyoxyethylene nonylphenyl ether and polyoxyethylene laurylphenyl ether; wetting agents such as dialkyl sulfosuccinates; fixing agents such as carboxymethyl cellulose and polyvinyl alcohol; and disintegrators such as sodium lignin sulfonate and sodium lauryl sulfate can be used.

For example, in the case of wettable powders, a bulk powder is prepared by mixing the compound of formula (I) as an active ingredient, with a solid carrier, a surfactant, etc., and the bulk power can be applied after dilution to a prescribed concentration with water on use. In the case of emulsions, a bulk liquid of an emulsion is prepared by mixing the above compound as an active ingredient with a solvent, a surfactant, etc., and the bulk liquid can be applied after dilution to a prescribed concentration with water on use. In the case of dusts, a dust is prepared by mixing the above compound as an active ingredient with a solid carrier, etc. and can be applied as such. In the case of granules, a granule is prepared by mixing the above compound as an active ingredient with a solid carrier, a surfactant, etc., followed by granulation. The granule can be applied as such. The methods for preparing the above-described preparations of various forms are not limited to the above-described methods, and those skilled in the art can optionally select an appropriate method depending on the kind of the active ingredient, the purpose of application, and the like.

The method of use varies depending on the kind and extent of pests, and the kind, cultivation form, and growth state of target crops, trees, and the like, but against arthropods, gastropods, nematodes, and the like, the preparations may be generally applied in an amount of the active ingredient ranging from 0.1 to 1000 g, preferably 1 to 100 g, per 10 are to the place where damage by the pests occurs or where the occurrence of damage is predicted.

With regard to a specific method of application, the above wettable powders, wettable granules, aqueous solutions, emulsions, liquids, flowable agents including suspensions in water and emulsions in water, capsules, and the like may be diluted with water and sprayed onto crops, trees, and the like in an amount ranging from 10 to 1000 liter per 10 are depending on the kind, cultivation form, and growth state of target crops, trees, and the like. Furthermore, in the cases of dusts, granules, and aerosols, the preparations may be applied as such to crops, trees, and the like within the range described in the above method of use.

In the case that the target pests mainly damage crops, trees, and the like in soil, the wettable powders, wettable granules, aqueous solutions, emulsions, liquids, flowable agents including suspensions in water and emulsions in water, capsules, and the like may be, for example, diluted with water and applied generally in an amount ranging from 5 to 500 liter per 10 are. At that time, the preparations may be sprayed on the soil surface uniformly over the whole area to be applied or may be irrigated into soil. When the preparations are dusts or granules, the preparations as such may be sprayed on the soil surface uniformly over the whole area to be applied. Also, at the spraying or irrigation, the preparations may be applied only to the vicinity of seeds, crops, trees, and the like to be protected from the damage by pests or the soil may be turned over during or after the spraying to disperse the active ingredient mechanically.

The outbreak of disease and pests can be also suppressed over a long period of time by using the compound of the present invention for coating seeds and sowing them. As a specific method, seeds are coated with a wettable powder, sol or dust prepared so as to contain the compound of the present invention is coated around the wetted seeds. At that time, the wettable powder, sol or dust is preferably used in an amount of 1 to 1000 g, preferably 10 to 200 g, per 100 g of seeds. By sowing the coated seeds thus prepared in a usual manner, not only damage by pests in soil can be prevented, but also stems and leaves, flowers, and fruits of plants after their growth can be protected from damage by pests.

Moreover, as methods for using the compound of the present invention at sowing, the following methods are exemplified. A granule comprising the compound of the present invention is mixed with soil for sowing and the soil is placed in a nursery bed. At the time, the soil to which the granule is applied may be used only for bed soil for the nursery bed, the soil to which the granule is applied may be used only for covering soil of a nursery box, or the soil may be used for both of bed soil and covering soil. In this case, the granule is used in an amount of preferably 0.1 to 100 g, more preferably 1 to 50 g, per 1.0 kg of soil. Moreover, after bed soil is placed in a nursery bed, a granule comprising the compound of the present invention may be applied by a method of dispersing it around the place where seeds are sown or by a method of dispersing the granule onto the place covered with soil after sowing. In this case, the granule is generally used in an amount of preferably 1 to 1000 g, more preferably 10 to 100 g, per one box of a nursery box (usually, one box of the nursery box corresponds to 0.5 a at fixing planting). In this connection, a wettable powder, dust, or the like may be used in a similar applying method instead of the granule.

Furthermore, as methods for using the compound of the present invention from germination to fixing planting (greening period) as a box-applying agent, the following methods may be exemplified.

A granule comprising the compound of the present invention is applied to a nursery box by dispersing it. In general, the granule is generally used in an amount of preferably 1 to 1000 g, more preferably 10 to 100 g, per one box of a nursery box (usually, one box of the nursery box corresponds to 0.5 a at fixing planting).

Moreover, in the case of an emulsion, liquid or sol (flowable agent), and microcapsule preparation, they may be used by irrigating a nursery box as they are or after diluting them with water. In the case of a wettable powder, wettable granule, aqueous solution, and aqueous granule solution, they may be used by irrigating a nursery box after diluting them with water. In this case, they are generally used in an amount of preferably 1 to 1000 ml, more preferably 10 to 100 ml, per one box of a nursery box (usually, one box of the nursery box corresponds to 0.5 a at fixing planting).

In the case of protecting the above-described standing trees, fallen trees, processed timber, stored woods from the damage by pests such as termites or beetles, methods of spraying, injecting, irrigating or applying an oil solution, emulsion, wettable powder or sol, or spraying the agent in the form of a dust or granule are exemplified. In such cases, the pest control agent comprising the compound of the present invention as an active ingredient can be employed alone or in combination with or as a mixed preparation with other active compounds such as an insecticide, acaricide, nematicide, fungicide, repellant, and synergist.

Any amount of the active ingredient such as the compound of the present invention may be contained in the preparations but the content is usually in the range of 0.0001 to 95% by weight as total amount of the active ingredients. It is preferable to contain the active ingredient in an amount of 0.005 to 10% by weight in oil solutions, dusts, granules, and the like and in an amount of 0.01 to 50% by weight in emulsions, wettable powders, sols, and the like. Specifically, in the case of expelling or controlling termites or beetles, the preparations may be sprayed onto the surface of soil or timber and woods in an amount of 0.01 to 100 g per 1 $m^2$ as the amount of the active ingredient.

(B) Cases Such as Livestock Industry and Fisheries Industry

The pest control agent comprising the compound of the present invention as an active ingredient is effective for repelling, expelling, and controlling pests such as arthropods, nematodes, trematodes, cestoids, and protozoa, which are parasitic internally or externally to animals and pets raised in stock raising industry, fisheries, and homes and which give direct damage such as ingestion of skin or the like and blood-sucking or give damage such as disease-spreading, and the agent can be used for preventing and treating the diseases relating to theses pests.

Target animals include spinal animals such as livestock including cattle, sheep, goat, horse, swine, and the like and cultural fishes; pets and experimental animals such as domestic fowls, dog, cat, etc., rodents including mouse, rat, hamster, squirrel, etc., Carnivora including ferret, etc., fishes, and the like.

Among pests, examples of Arthropoda Insecta and Arachnida are described below. Examples of Diptera include Tabanidae such as *Chxysops japonica, Simulium iwatens*, and *Tabanus trigonus*; Muscidae such as *Ophyra leucostoma, Musca domestica*, and *Stomoxys calcitrans*; Gasterophilidae such as *Gasterophilus intestinalis*; Hypodermidae such as *Hypoderma bovis*; Calliphoridae such as *Phaenicia cuprina*; Phoridae such as *Megaseria spiracularis*; Sepsidae such as *Sepsis monostigma*; Psychodidae such as *Telmatoscopus albipunctatus* and *Psychoda alternata*; Culicidae such as *Anopheles hyrcanus sinensis, Culex tritaeniorhynchus*, and *Aedes albopictus*; Simuliidae such as *Prosimulium hirtipes*; Ceratopogonidae such as *Culicoides oxystoma* and *Culicoides arakawai*; and the like.

Examples of Siphonaptera include Pulicidae such as *Ctenocephalides felis* and *Ctenocephalides canis*, and the like.

Examples of Anoplura include Echinophthiriidae such as *Haematopinus suis* and *Haematopinus eurysternus*; Trichodectidae such as *Damalinia equi*; Linognathidae such as *Linognathus vituli*; Menoponidae such as *Menopon gallinae*; and the like.

Examples of Arthropoda Arachnida Acarina include Ixodidae such as *Haemaphysalis longicornis, Ixodes ovatus, Boophilus microplus,* and *Amblyomma testudinarium*; Macronyssidae such as *Ornithonyssus sylviarum*; Dermanyssidae such as *Dermanyssus gallinae*; Demodicidae such as *Demodex suis*; Sarcoptidae such as *Notoederes cati* and *Sarcoptes sylvianum*; Psoroptidae such as *Otodectes cynotis* and *Psoroptes bovis*; and the like.

Examples of Nematoda Phasmidia are described below.

Examples of Strongylida include Ancylostoma, Stephanurus dentatus, Metastrongylus elongatus, Trichostrongylus, Oesophagostomum, and the like. Examples of Ascarida include Ascarus lumbricoides, Parascaris equorum, and the like.

Examples of Platyhelminthes Trematoda include Schistosoma japonicum, Fasciola hepatica, Paramphistomum cervi, Paragonimus westermanii, Prosthogonimus japonicus, and the like.

Examples of Cestoda include Anoplocephala perfoliata, Moniezia expansa, Moniezia benedeni, Raillietina tetragona, Raillietina sp., Raillietina cesticillus, and the like.

Examples of Protozoa Mastigophora include Histomonas and the like as *Rhizomastigida; Leishmania, Trypanosoma,* and the like as *Tripanpsomidae; Giardia* and the like as *Polymastigida;* and *Trichomonas* and the like as *Trichomonadia*.

Furthermore, examples of Sarcodina Amoebida include *Entamoeba* and the like. Examples of Sporozoa Piroplasmea include Theilaria, Babesia and the like. Examples of Telosporidia include Eimeria, Plasmodium, Toxoplasma, and the like.

The pest control agent comprising the compound of the present invention as an active ingredient can be employed as any preparation or any usable form prepared by formulation effective on the above agricultural or forestry cases, alone or in combination with or as a mixed preparation with other active compounds such as an insecticide, acaricide, nematicide, fungicide, synergist, plant regulator, herbicide, and toxic feed. The substances mentioned in the article of "(A) Cases such as agriculture and forestry" are exemplified as specific examples of the above other active compounds, but they are not limited thereto.

The specific application methods include incorporation into feeds of livestock, pets, and the like; oral administration as a suitable orally-ingestible formulated composition, e.g., a tablet, pill, capsule, paste, gel, drink, medicated feed, medicated drink, medicated additional feed, sustained release large pill, or sustained release device so as to be retained in gastrointestinal tracts containing a pharmaceutically acceptable carrier and coating substance; and percutaneous application as a spay, powder, grease, cream, ointment, emulsion, lotion, preparation for spot-on, preparation for pour-on, shampoo, or the like.

As the methods for percutaneous application and topical application, devices (e.g., collars, medallions, and ear-tags) attached to animals so as to control arthropods topically or systemically may be utilized.

Specific methods for oral administration and percutaneous application in the case of use as anthelmintics for livestock and pets are described below, but in the present invention, the methods of application are not limited thereto.

In the case of oral administration as a medicated drink, a suspension or dispersion may be usually formed by dissolving an active ingredient into an appropriate nontoxic solvent or water together with a suspending agent such as bentonite, a wetting agent, or other excipients, and an antifoaming agent may be contained, if necessary. The drink generally contains the active ingredient in an amount of 0.01 to 1.0% by weight, preferably 0.01 to 0.1% by weight.

In the case of oral administration as unit usable forms of dry solid, a capsule, pill, or tablet containing a predetermined amount of the active ingredient is usually employed. These usable forms may be prepared by mixing the active ingredient homogeneously with a suitably pulverized diluent, filler, disintegrator, and/or binders, such as starch, lactose, talc, magnesium stearate, plant gum, and the like. At the formulation of such unit usable forms, the quantity and content of an anthelmintic may be optionally determined depending on the kind of host animal to be treated, the extent of infection, the kind of parasite, and the body weight of the host.

In the case of administration as a feed, there may be mentioned methods wherein the compound of the active ingredient is homogeneously dispersed in the feed, the agent is employed as top-dressing or in a form of pellet. For achieving an anthelmintic effect, the compound of the active ingredient is contained in the final feed in an amount of 0.0001 to 0.05% by weight, preferably 0.0005 to 0.01% by weight.

In the case of a solution or dispersion in a liquid carrier excipient, the preparations may be administered parenterally to animals by injection to proventriculus, or intramuscular, endotracheal, or subcutaneous injection. Because of parenteral administration, the compound of the active ingredient is preferably mixed with a vegetable oil such as peanuts oil or cottonseed oil. In such formulation, the compound of the active ingredient is generally contained in an amount of 0.05 to 50% by weight, preferably 0.1 to 0.2% by weight.

Moreover, the preparation mixed with a carrier such as an aliphatic alcohol, a hydrocarbon solvent, or the like can be applied directly and topically to the outer surface of livestock or pets by spraying or direct pouring. In such formulation, the compound of the active ingredient is generally contained in an amount of 0.05 to 50% by weight, preferably 1 to 20% by weight. Also, in this case, in order to prevent the precipitation of the active ingredient, it is preferable to contain crystallization-inhibiting agents such as surfactants and film-forming agents.

By containing the active ingredient in a parent material of pest-controlling goods such as collar and ear-ring, it can be also administered indirectly to livestock and pets. At that time, the compound of the active ingredient is generally contained in an amount of about 0.1 to 40% by weight, preferably about 1 to 15% by weight. The parent material may be optionally selected depending on the usable forms, and examples include molded articles of thermoplastic resins such as vinyl chloride resin and fabric articles produced from textile products such as cotton and polyesters.

(C) Cases Such as Public Health

The pest control agent comprising the compound of the present invention as an active ingredient is also effective for repelling, expelling, and controlling pests on cases for public health which adversely affect the environment of food, clothing and shelter, or further damage human bodies or transporting or carrying pathogens, for the purpose of keeping public health conditions. Specifically, the pest control agent of the present invention is effective for repelling, expelling, and controlling lepidopteran, beetles, bookworms, cockroaches, flies, and mites which damage houses themselves and indoor or outdoor timber, wood products such as wood furniture, stored foods, clothes, books, animal goods (leather, fur, wool, feathers, etc.), plant goods (clothes, paper, etc.), and the like, and adversely affect healthy life. Specific examples of pests on such public health cases are described below.

Examples of Arthropoda Insecta are described below. Examples of Lepidoptera include Lymantriidae such as *Euproctis similis*; Lasiocampidae such as *Dendrolimus undans flaveola*; Heterogeneidae such as *Parasa consocia*; Zygaenidae such as *Artona funeralis*; Pyralidae such as *Cadra cautella, Ephestia cautella*, and *Plodia interpunctella*; Gelechiidae such as *Sitotroga cerearella*; Tineidae such as *Tinea pellionella* and *Tineola bisselliella*; and the like.

Examples of Coleoptera include Oedemeridae such as *Xanthochroa waterhousei*; Meloidae such as *Epicauta gorhani*; Staphylinidae such as *Paederus fuscipes*; Rhynchophoridae such as *Sitophilus zeamais* and *Sitophilus oryzae*; Bruchidae such as *Callosobruchus chinensis, Bruchus pisorum*, and *Bruchus rufimanus*; Tenebrionidae such as *Tribolium castaneum*; Cucujidae such as *Oryzoephilus surinamensis* and *Placonotus testaceus*; Anobiidae such as *Lasioderma serricorne* and *Stegobium paniceum*; Dermestidae such as *Attagenus unicolor, Anthrenus verbasci*, and *Dermestes maculatus*; Ptinidae such as *Gibbium aequinoctiale*; Bostrychidae such as *Dinoderus minutus* and *Rhizopertha dominica*; Lyctidae such as *Lyctus brunneus*; and the like.

Examples of Hymenoptera include Vespidae such as *Vespa mandarinia*; Formicidae such as *Brachyponera chinensis*; Pompilidae such as *Batozonellus annulatus*; and the like.

Examples of Diptera include Culicidae such as *Aedes jaonica*; Ceratopogonidae such as *Culicoides* sp.; Chironomidae such as *Chironomus dorsalis*; Simuliidae such as *Simulium aokii*; Tabanidae such as *Chrysops japonicus*; Muscidae such as *Musca domestica*; Anthonmyiidae such as *Fannia canicularis*; Calliphoridae such as *Phormia regina*; Sarcophagidae such as *Boettcherisca peregrina*; Drosophilidae such as *Drosophila virilis*; Piophilidae such as *Piophila casei*; and the like.

Examples of Siphonaptera include Pulicidae such as *Pulex irritans*, and the like.

Examples of Collembola include Neogastruridae such as *Neogastruna communis*, and the like.

Examples of Blattaria include Blattellidae such as *Blattela germania* and *Asiablatta kyotensis*; Blattidae such as *Periplaneta americana, Periplaneta fuliginosa*, and *Periplaneta japonica*; and the like.

Examples of Orthoptera include Gryllacridoidea such as *Diestrammena japonica* and Steropelmatidae, and the like.

Examples of Anoplura include Pediculidae such as *Pediculus humanus capitis*; Pthiridae such as *Pthirus pubis*; and the like.

Examples of Hemiptera include Cimicidae such as *Cimex lectularius*; Reduriidae such as *Isyndus obscurus*; and the like.

Examples of Isoptera include Phinotermitidae such as *Reticulitermes speratus* and *Coptotermes formosanus*; Kalotemitidae such as *Cryptotermes domesticus*; and the like. Examples of Psocoptera include Trogiidae such as *Lepinotus reticulatus*; tiposcelidae such as *Liposcelis bostrichophilus*; and the like. Examples of Thysanura include Lepismatidae such as *Ctenolepisma villosa* and *Lepisma saccharina*, and the like.

Examples of Arthropoda Arachnida are described below.

Examples of Acarina include Ixodidae such as *Ixodes persulcatus*; Macronyssidae such as *Ornithonyssus bacoti*; Cheyletidae such as *Chelacaropsis moorei*; Pyemotidae such as *Pyemotes tritici*; Demodicidae such as *Demodex folliculorum*; Pyroglyphidae such as *Permatophagoides pteronyssius*; Sarcoptidae such as *Sarcoptes scabiei*; Trombiculidae such as *Leptotrombidum akamushi*; Acaridae such as *Tyrophagus putrescentiae* and *Lardoglyphus konoi*; Carpoglyphidae such as *Carpoglyphus lactis*; and the like.

Examples of Araneae include Clubionidae such as *Chiracanthium japonicum*; Heteropodidae such as *Heteropoda venatoria*; Pholcidae such as *Spermophora senoculata* and *Pholcus phalangioides*; Urocteidae such as *Uroctea conpactilis*; and Salticidae such as *Plexippus paykulli* and *Plexippus setipes*; and the like.

Examples of Scorpiones include Buthidae such as *Isometrus europaeus*, and the like.

As other Arthropoda, examples of Chilopoda Scolopendromorpha include Scolopendridae such as *Scolopendra subspinipes* and *Otostigmus multispinosus*, and the like. Examples of Scutigeromorpha include Scutigeridae such as *Thereuonema hilgendorfi*, and the like. Moreover, examples of Arthropoda Diplopoda Polydesmoidea include Strongylosomidae such as *Oxidus gracilis*, and the like. Examples of Arthropoda Crustacea Isopoda include Oniscidae such as *Porcellio scaber*, and the like. Furthermore, examples of Annelida Hirudinea Gnathobdellida include Haemadipsidae such as *Haemadipsa zeylanica japonica*, and the like.

The pest control agent comprising the compound of the present invention as an active ingredient can be employed as any preparation or any usable form prepared by formulation effective on the above public health cases, alone or in combination with or as a mixed preparation with other active compounds such as an insecticide, acaricide, nematicide, fungicide, synergist, plant regulator, herbicide, and toxic feed. The substances mentioned in the article of "(A) Cases such as agriculture and forestry" are exemplified as specific examples of the above other active compounds, but they are not limited thereto.

The usable form of the pest control agent of the present invention may be any form and the protection of the above animal goods or plant goods can be achieved by spraying an oil solution, emulsion, wettable powder, dust, or the like, placing a resin steam-fogging agent, treating with a smoking agent or aerosol, placing a granule, tablet, or toxic feeds, spraying an aerosol, or the like. The compound of the active ingredient is preferably contained in the preparations in an amount of 0.0001 to 95% by weight.

Examples of application method, against pests, for example, directly damaging arthropods, disease-carrying arthropods, and the like include methods of spraying, injecting, irrigating, and applying an oil solution, emulsion, wettable powder, or the like, spraying a dust or the like, treating with a preparation such as a fumigant, mosquito coil, heat aerosol including self-combustion type smoking agent or chemically reactive aerosol, smoking agent including fogging, or ULV agent, and others. Also, a granule, tablet, or toxic feed, for example, may be placed as other form, or a floating dust, granule, or the like may be applied by adding them dropwise into waterways, wells, reservoirs, water tanks, and other running water or retained water.

Furthermore, Euproctis which is also a pest in agriculture and forestry can be controlled in a similar manner to the methods described in the article of "(A) Cases such as agriculture and forestry". A method of incorporating the control agent into the feed of livestock so that the dung is contaminated with the active ingredient is effective against flies, and a method of vaporization into air with an electric mosquito coil is also effective against mosquitoes.

The preparations which are useable forms thereof may be present as mixed preparations together with the above-described other active compound such as an insecticide, acaricide, nematicide, fungicide, repellant, or synergist, and the compound of the active ingredient is preferably contained in these preparations in an amount of 0.0001 to 95% by weight in total. In this connection, it is also possible to use the preparations in combination with other active compounds on use.

In the case of protecting houses, wood furniture, and the like from damage by pests such as termites or beetles, there may be mentioned methods of spraying, injecting, irrigating, or applying an oil solution, emulsion, wettable powder or sol, or spraying the agent in the form of a dust or granule toward houses, wood furniture, and the like and vicinity thereof. In such cases, the compound of the present invention can be also employed alone or in combination with or as a mixed preparation with other active compounds such as an insecticide, acaricide, nematicide, fungicide, repellant, and synergist.

Any amount of the compound of the active ingredient such as the compound of the present invention may be contained in the preparations but the content is usually in the range of 0.0001 to 95% by weight as a total amount of the active ingredients. It is preferable to contain the compounds in an amount of 0.005 to 10% by weight in oil solutions, dusts, granules, and the like and in an amount of 0.01 to 50% by weight in emulsions, wettable powders, sols, and the like. Specifically, in the case of expelling or controlling termites or beetles, the preparations may be sprayed to the vicinity or directly onto the surface in an amount of 0.01 to 100 g per 1 $m^2$ as the amount of the compound of the active ingredient.

At repelling, expelling, and controlling pests which damage human bodies or transport or carry pathogens, other than the above-described methods, there may be mentioned oral administration as a suitable orally-ingestible formulated composition, e.g., a tablet, pill, capsule, paste, gel, drink, medicated feed, medicated drink, medicated additional feed, sustained release large pill, or sustained release device so as to be retained in gastrointestinal tracts containing a pharmaceutically acceptable carrier and coating substance; and percutaneous application as spay, powder, grease, cream, ointment, emulsion, lotion, preparation for spot-on, preparation for pour-on, shampoo, or the like.

Specific formulation can be carried out in a similar manner to the methods described in the articles of "(B) Cases such as livestock industry and fisheries industry".

EXAMPLES

The present invention is explained in further detail with reference to Examples but the present invention is not limited to the following Examples unless it exceeds the gist thereof.

Example 1

Production of 1-(2,6-dichloro-4-trifluoromethylphenyl)-4-fluoromethylthio-5-(pyridin-4-ylmethylamino)pyrazole-3-carbonitrile (Compound No. 1)

To a mixture of 7.7 g of 5-amino-1-(2,6-dichloro-4-trifluoromethylphenyl)-4-fluoromethylthiopyrazole-3-carbonitrile, 2.2 g of 4-pyridinecarboxyaldehyde, 80 ml of toluene and 0.1 g of p-toluenesulfonic acid monohydrate was added, followed by heating under reflux for 10 hours while the resulting water was removed. After cooling to room temperature, 30 ml of ice-water was added thereto, followed by extraction. The organic layer was dried over anhydrous sodium sulfate. The solvent was removed by distillation under reduced pressure to thereby obtain crude 1-(2,6-dichloro-4-trifluoromethylphenyl)-4-fluoromethylthio-5-(pyridin-4-ylmethylideneimino)pyrazole-3-carbonitrile.

To a methanol (100 ml) solution of the thus obtained 1-(2,6-dichloro-4-trifluoromethylphenyl)-4-fluoromethylthio-5-(pyridin-4-ylmethylideneimino)pyrazole-3-carbonitrile, 0.4 g of sodium borohydride was gradually added. After stirring at room temperature for 1 hour, ice and ethyl acetate were added thereto, followed by extraction. The organic layer was washed with saturated saline and then dried over anhydrous sodium sulfate. The residue was purified by silica gel column chromatography to thereby obtain 7.6 g of the compound (No. 1) described in the following Table 1.

Melting point: 204° C. $^1$HNMR (CDCl$_3$): 4.41 (2H, d), 4.68 (1H, t), 5.39 (1H, s), 5.56 (1H, s), 7.04 (2H, d), 7.67 (2H, s), 8.49 (2H, d)

Example 2

Production of 1-(2,6-dichloro-4-trifluoromethylphenyl)-4-difluoromethylthio-5-(pyridin-2-ylmethylamino)pyrazole-3-carbonitrile (Compound No. 2)

To a mixture of 8.0 g of 5-amino-1-(2,6-dichloro-4-trifluoromethylphenyl-4-difluoromethylthiopyrazole-3-carbonitrile, 2.2 g of 2-pyridinecarboxyaldehyde, 60 ml of toluene and 20 mg of p-toluenesulfonic acid monohydrate were added, followed by heating under reflux for 3 hours while the resulting water was removed. After cooling to room temperature, 0.1 ml of triethylamine and 30 ml of ice-water were added thereto, followed by extraction. The organic layer was dried over anhydrous sodium sulfate. The solvent was removed by distillation under reduced pressure to thereby obtain crude 1-(2,6-dichloro-4-trifluoromethylphenyl)-4-difluoromethylthio-5-(pyridin-2-ylmethylideneimino)pyrazole-3-carbonitrile.

To a methanol (50 ml) solution of the thus obtained 1-(2,6-dichloro-4-trifluoromethylphenyl)-4-difluoromethylthio-5-(pyridin-2-ylmethylideneimino)pyrazole-3-carbonitrile, 0.7 g of sodium borohydride was gradually added. After stirring at room temperature for 1 hour, ice and ethyl acetate were added thereto, followed by extraction. The organic layer was washed with saturated saline and then dried over anhydrous sodium sulfate. The residue was purified by silica gel column chromatography to thereby obtain 8.4 g of the compound (No. 2) described in the following Table 1.

Melting point: 117-120° C. $^1$HNMR (CDCl$_3$): 4.57 (2H, d), 5.88 (1H, m), 6.73 (1H, t), 7.19 (2H, t), 7.66 (1H, t), 7.77 (2H, s), 8.41 (1H, d)

Example 3

The compounds shown in Table 1 were synthesized in accordance with the methods described in Examples 1 and 2.

Compound Nos. and NMR data are shown below.

No. 3:
$^1$HNMR (CDCl$_3$): 4.47 (2H, d), 4.67 (1H, bs), 6.69 (1H, t) 7.05 (2H, d), 7.68 (2H, s), 8.51 (2H, d)

No. 4:
$^1$HNMR (CDCl$_3$): 3.25 (2H, q), 4.44 (2H, d), 4.67 (1H, t), 7.04 (2H, d), 7.64 (2H, s), 8.48 (2H, d)

TABLE 1

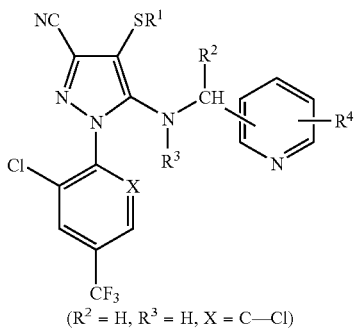

($R^2$ = H, $R^3$ = H, X = C—Cl)

| Compound No. | SR$^1$ | R$^4$ | Substitution position of pyridine | m.p. (° C.) |
|---|---|---|---|---|
| 1 | SCH$_2$F | H | 4- | 204 |
| 2 | SCHF$_2$ | H | 2- | 117-120 |
| 3 | SCHF$_2$ | H | 4- | 127-131 |
| 4 | SCH$_2$CF$_3$ | H | 4- | 164-167 |

Production Example 1

Production of 1-(2,6-dichloro-4-trifluoromethylphenyl)-5-(pyridin-2-ylmethylamino)pyrazole-3-carbonitrile (1) To a three-neck flask, 40 ml of dried toluene, 10 g (31.1 mmol) of 1-(2,6-dichloro-4-trifluoromethylphenyl)-5-aminopyrazole-3-carbonitrile, 4.55 g of 2-pyrinecarboxyaldehyde and 0.03 g of p-toluenesulfonic acid were charged, followed by refluxing under nitrogen for 3 hours. After the above reaction solution was washed with water three times, the organic phase was dried over magnesium sulfate. Then, magnesium sulfate was -removed by filtration and the solvent was removed by distillation to thereby obtain 12.63 g of 1-(2,6-dichloro-4-trifluoromethylphenyl)-5-(pyridin-2-ylmethylideneimino)pyrazole-3-carbonitrile as a solid purity: 98.6 LC%, 30.3 mmol, yield: 97.3%).

(2) To a three-neck flask, 2000 ml of dried methanol, 47.7 g (purity: 96%, 109.9 mmol) of 1-(2,6-dichloro-4-trifluoromethylphenyl)-5-(pyridin-2-ylmethylideneimino)pyrazole-3-carbonitrile and 2.0 g of sodium tetrahydroborate were charged, followed by reaction under nitrogen for 2 hours. Thereafter, the crystals formed in the reaction solution were collected by filtration, washed with water and methanol, and then dried in vacuo to thereby obtain 42.84 g of 1-(2,6-dichloro-4-trifluoromethylphenyl)-5-(pyridin-2-ylmethylamino)pyrazole-3-carbonitrile as a solid (purity: 97.5%, 101.3 mmol, yield: 84.1%).

Production Example 2

Production of bis[1-(2,6-dichloro-4-trifluoromethylphenyl)-3-cyano-5-(pyridin-2-ylmethylamino)pyrazol-4-yl] disulfide To a test tube, 1 ml of acetic acid, 3 ml of dried toluene, 200 mg (0.485 mmol) of 1-(2,6-dichloro-4-trifluoromethylphenyl)-5-(pyridin-2-ylmethylamino)pyrazole-3-carbonitrile and 40 mg of sulfur monochloride (S$_2$Cl$_2$) were charged, followed by reaction under nitrogen for 3 hours. Thereafter, the crystals formed in the reaction solution were collected by filtration, neutralized with an aqueous sodium bicarbonate solution, and extracted with ethyl acetate, followed by liquid phase separation. After the organic phase was dried over magnesium sulfate, magnesium sulfate was filtered off and ethyl acetate was removed by distillation to thereby obtain 200 mg of bis[1-(2,6-dichloro-4-trifluoromethylphenyl)-3-cyano-5-(pyridin-2-ylmethylamino)pyrazol-4-yl)] disulfide (purity: 85.6%, 0.193 mmol, yield: 79.7%).

Example 4

Production of Compound No. 2 Using Chlorodifluoromethane

To a 50 mL three-neck flask, 500 mg (0.565 mmol) of bis[1-(2,6-dichloro-4-trifluoromethylphenyl)-3-cyano-5-(pyridin-2-ylmethylamino)pyrazol-4-yl] disulfide obtained by the method of Production Example 2 and absolute ethanol (15 mL) were charged under a nitrogen atmosphere, followed by cooling to 3° C. Sodium borohydride (64 mg, 3.0 eq.) was gradually added thereto under stirring. The mixture was allowed to stand to room temperature and stirred for 1 hour. Subsequently, while blowing chlorodifluoromethane into the reaction solution using a gas-inlet tube, sodium ethoxide (192 mg, 2.83 mmol, 5.0 eq.) dissolved in 5 ml of absolute ethanol was gradually added dropwise into the reaction solution. After the reaction was completed, ethanol was removed by distillation and 20 mL of distilled water was added thereto, followed by extraction with ethyl acetate (75 mL×2). The ethyl acetate extracts were combined and the combined extract was washed with distilled water (30 mL) and dried over anhydrous magnesium sulfate. After magnesium sulfate was filtered off, ethyl acetate was removed by distillation to thereby obtain 1-(2,6-dichloro-4-trifluoromethylphenyl)-4-difluoromethylthio-5-(pyridin-2-ylmethylamino)pyrazole-3-carbonitrile in 64% yield.

Example 5

Production of Compound No. 2 Using Difluoromethylsulfenyl Chloride

Under a nitrogen atmosphere, 500 mg (1.21 mmol) of 1-(2,6-dichloro-4-trifluoromethylphenyl)-5-(pyridin-2-ylmethylamino)pyrazole-3-carbonitrile was suspended into 5.0 mL of dried dichloromethane, and 2.0 mL of dried dichloromethane containing 180 mg (1.52 mmol, 1.25 eq.) of difluoromethylsulfenyl chloride was added dropwise thereto under stirring at room temperature, followed by reaction for 2 hours. Ethyl acetate (100 mL) was added thereto, and the organic layer was washed successively with 20 mL of a saturated aqueous sodium hydrogen carbonate solution and 20 mL of water, followed by drying over anhydrous magnesium sulfate. After magnesium sulfate was filtered off, the solvent was removed by distillation under reduced pressure and the crude product was recrystallized from a mixed solvent of hexane/ethyl acetate (3/1) to thereby obtain 535 mg of 1-(2,6-dichloro-4-trifluoromethylphenyl)-4-difluoromethylthio-5-(pyridin-2-ylmethylamino)pyrazole-3-carbonitrile (yield: 90%, purity: 96%).

Formulation Examples of the agricultural and horticultural insecticides comprising the compound of the present invention as an active ingredient are shown below, but the usable forms of the present invention are not limited thereto.

Formulation Example 1

Wettable Powder

Twenty parts by weight of the compound of the present invention, 20 parts by weight of Carplex #80 (white carbon, manufactured by Shionogi & Co., Ltd., trade name) 52 parts by weight of ST Kaolin Clay (kaolinite, manufactured by Tsuchiya Kaolin K.K., trade name), 5 parts by weight of Sorpol 9047K (anionic surfactant, manufactured by Toho Chemical Industry Co., Ltd., trade name) and 3 parts by weight of Runox P65L (anionic surfactant, manufactured by Toho Chemical Industry Co., Ltd., trade name) were mixed and ground uniformly to thereby obtain a wettable powder containing 20% by weight of the active ingredient.

Formulation Example 2

Dust

Two parts by weight of the compound of the present invention, 93 parts by weight of clay (manufactured by Nippon Talc K.K.) and 5 parts by weight of Carplex #80 (white carbon, manufactured by Shionogi & Co., Ltd., trade name) were uniformly mixed and ground to thereby obtain a dust containing 2% by weight of the active ingredient.

Formulation Example 3

Emulsion

In a mixed solvent of 35 parts by weight of xylene and 30 parts by weight of dimethylformamide, 20 parts by weight of the compound of the present invention was dissolved, and 15 parts by weight of Sorpol 3005X (mixture of a nonionic surfactant and an anionic surfactant, manufactured by Toho Chemical Industry Co., Ltd., trade name) was added thereto to thereby obtain an emulsion containing 20% by weight of the active ingredient.

Formulation Example 4

Flowable Agent

Thirty parts by weight of the compound of the present invention, 5 parts by weight of Sorpol 9047K, 3 parts by weight of Sorbon T-20 (nonionic surfactant, manufactured by Toho Chemical Industry Co., Ltd., trade name), 8 parts by weight of ethylene glycol and 44 parts by weight of water were mixed and ground in Dynomill (manufactured by Shinmaru Enterprises Co.). To the resulting mixture slurry, 10 parts by weight of a 1 wt % aqueous solution of xanthan gum (a natural polymer) was added, followed by mixing and grinding thoroughly to thereby obtain a flowable agent containing 20% by weight of the active ingredient.

Formulation Example 5

Granule

Two parts of the compound of the present invention, 40 parts of bentonite, 53 parts of clay, and 5 parts of calcium lignin sulfonate were uniformly mixed and ground. After water was added and the resulting mixture was thoroughly kneaded together, the product was extruded and granulated and the resulting product was dried and sized to thereby obtain a granule.

Formulation Example 6

Granule

After silica sand was placed in a rolling granulator and wetted, 2 parts of the compound of the present invention, 3 parts of calcium lignin sulfonate, 0.5 part of polyvinyl alcohol (PVA), 0.5 part of white carbon, and 94 parts of silica sand which had been mixed and grounded beforehand were charged thereto to effect coating, and then the resulting product was dried and sized to thereby obtain a granule.

Formulation Example 7

Granule Seeds Coated with Dust

A dust prepared by uniformly mixing and grinding 2 parts of the compound of the present invention, 6 parts of calcium lignin sulfonate, 10 parts of polyvinyl alcohol, and 82 parts of clay was mixed with seeds wetted beforehand, and the mixture was air-dried to thereby obtain coated seeds.

Test Examples of the agricultural and horticultural insecticides comprising the compound of the present invention as an active ingredient are shown below, but the usable forms are not limited thereto.

Test Example 1

Insecticidal Effect on Larvae of Brown Rice Planthopper (Nilaparvata lugens)

A rice seedling was planted in a glass cylinder (inner diameter: 3 cm×length: 17 cm), and five 4th instar larvae of *Nilaparvata lugens* were set free therein. An agricultural and horticultural insecticide of the present invention was prepared in accordance with Formulation Example 3 and diluted with water, and 0.5 ml of the resulting dilution was sprayed into the above glass cylinder with a spraying tower (manufactured by Mizuho Rika) (duplicates at a concentration). The cylinder was kept in a constant temperature room at 25° C., and the mortality and agony of the larvae were investigated after 5 days from the treatment to obtain a death rate (%) taking an agonizing insect as a ½ dead insect. The results obtained are shown in Table 2 (the compound numbers in the table correspond to the numbers in Table 1).

TABLE 2

| Compound No. | Concentration (ppm) | Death rate (%) |
| --- | --- | --- |
| 1 | 500 | 100 |
| 2 | 500 | 100 |
| 3 | 500 | 100 |
| 4 | 500 | 100 |

Test Example 2

Insecticidal Effect on Larvae of Diamond Back Moth (*Plutella xylostella*)

A disc (diameter: 6 cm) cut out of a cabbage leaf was for 1 minute in an aqueous dilution of the agricultural and horticultural insecticide of the present invention prepared in accordance with Formulation Example 1, then air-dried, and placed in a plastic cup (inner diameter: 7 cm). Five 3-instar larvae of *Plutella xylostella* were set free in the cup (duplicates at a concentration). The cup was kept in a constant temperature room at 25° C., and the death and agony of the larvae were investigated after 4 days from the treatment to obtain a death rate (%) taking an agonizing insect as a ½ dead insect. The results are shown in Table 3 (the compound numbers in the following table below correspond to the numbers in Table 1).

TABLE 3

| Compound No. | Concentration (ppm) | Death rate (%) |
| --- | --- | --- |
| 1 | 500 | 100 |
| 2 | 500 | 100 |
| 3 | 500 | 100 |
| 4 | 500 | 100 |

Test Example 3

Insecticidal effect on imagoes of adzuki bean weevil (*Callosobruchus chinensis*)

Two adzuki beans were put in a glass cylinder (inner diameter: 3 cm×length: 15 cm), and 10 imagoes of *Callosobruchus chinensis* were set free therein. An agricultural and horticultural insecticide of the present invention was prepared in accordance with Formulation and diluted with water, and 0.3 ml of the resulting dilution was sprayed in the above glass cylinder with a spray tower (manufactured by Mizuho Rika) (duplicates at a concentration). The cylinder was kept in temperature room at 25° C., and the mortality and agony of thee larvae were investigated after 4 days from the treatment to obtain a death rate (%) taking an agonizing insect as a ½ dead insect. The results obtained are shown in Table 4 (the compound numbers in the table correspond to the numbers in Table 1).

TABLE 4

| Compound No. | Concentration (ppm) | Death rate (%) |
| --- | --- | --- |
| 1 | 500 | 100 |
| 2 | 500 | 100 |
| 3 | 500 | 100 |
| 4 | 500 | 100 |

Test Example 4

Insecticidal Effect on Larvae of Green Peach Aphid (*Myzus persicae*)

Water was put in a screw bottle (volume: 10 ml), and a leaftalk of Japanese radish was placed therein and then inoculated with 5 to 6 insects of Myzus persicae per leave. After the inoculation, the bottle was put in a glass cylinder (diameter: 3.5 cm; height: 15 cm, with a mesh cover), and the insects were let to proliferate in a constant temperature room kept at 25° C. for 3 days. The imagoes on the leaves were removed, and the leaves were soaked in an aqueous dilution of an agricultural and horticultural insecticide of the present invention prepared in accordance with Formulation Example 3 (for about 5 seconds) and then returned into the glass cylinder (duplicates at a concentration). The cylinder was kept in the constant temperature room at 25° C., and the number of the insects on the leaves was counted on the 4th day after the treatment to obtain a death rate (%) based on the results. The results obtained are shown in Table 5 (the compound numbers in the table correspond to the numbers in Table 1).

TABLE 5

| Compound No. | Concentration (ppm) | Death rate (%) |
| --- | --- | --- |
| 1 | 500 | 100 |
| 2 | 500 | 100 |
| 3 | 500 | 100 |
| 4 | 500 | 100 |

Test Example 5

Insecticidal Effect on Larvae of Brown Rice Planthopper (*Nilaparvata lugens*) through Systemic Activity Roots of young rice seedlings (height: about 10 cm) planted in a plastic cup were washed with water and soil was washed away so as not to damage the fine roots. The stem was pinched by a urethane tip (diameter: 3 cm, height: 2 cm) having a cut line and the roots were inserted into an Erlenmeyer flask to which 50 ml of an agent solution (an aqueous dilution of the agricultural and horticultural insecticide of the present invention prepared in accordance with Formulation Example 1) was placed beforehand (2 to 3 young rice seedlings/flask). The urethane chip was wedged into the mouse of the flask to fix the rice seedlings. A glass tube (diameter: 3 cm, height: 5 cm) was placed thereon, wedged into the urethane chip, and fixed with a tape. The flask in such state was kept in a constant temperature room at 25° C. for 3 days. Five larvae of *Nilaparvata lugens* were placed in the glass tube and then the tube was capped with a urethane chip, followed by keeping in the constant temperature room at 25° C. (duplicates at a concentration). The mortality and agony of the larvae were investigated on 4th day after the treatment to obtain a death rate (%) taking an agonizing insect as a ½ dead insect. This test was carried out on two agent solutions different in the concentration of the active ingredient. The results are shown in Table 6 (the compound numbers in the table correspond to the numbers in Table 1).

Additionally, as reference compounds, Compounds I, II and III described in JP-A-10-338676 were similarly tested.

TABLE 6

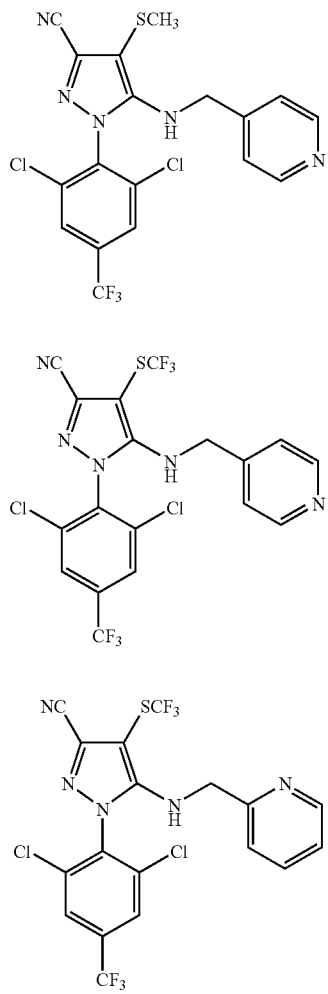

| Compound No. | Death rate (%) 3.1 ppm | 0.8 ppm |
|---|---|---|
| 1 | 100 | 100 |
| 2 | 100 | 100 |
| 3 | 100 | 100 |
| I | 100 | 100 |
| II | 50 | 20 |
| III | 0 | 0 |

Brown rice planthopper (*Nilaparvata lugens*) is a highly problematic pest insect species in agricultural and horticultural cases, but a sufficient effect cannot be attained by the application method of spraying an agent to stems and leafs, provided that the detection is delayed or that an enough amount of the agent is not spread to the roots.

Since this species has a characteristic of making its habitat around the roots of rice plant or the like and harming the plant through sucking fluid, more efficient method of controlling the insect may be a method of treating the surface of soil with an agent (granule treatment) before the outbreak of the species occurs widely. However, in order to attain a high controlling effect by such a method, a penetrating and migrating property (systemic property) into a plant body is required as the nature of the agent. As is apparent from Table 6, all of the compounds of the present invention and Compound I exhibited an insecticidal activity through a high systemic property against this species of a highly problematic pest insect. On the other hand, Compounds II and III exhibited an obviously inferior effect owing to its lower property than the compounds of the present invention.

Test Example 6

In Vitro Intercellular Metabolic Cooperation Inhibition Test (IMC)

In this Test Example, using an inhibitory action of gap-junctional intercellular communication as an index, the existence of carcinogenicity (tumor-promoting action) of a compound was investigated.

In this test, a mixed culture system of Chinese hamster lung fibroblast line V79 (hgprt+) having hypoxanthine-guanine phosphoribosyltransferase activity and cells having no such activity (hgprt−) was treated by adding thereto the following compounds together with 6-thioguanine (6-TG). When the intercellular communication is normal, the toxic metabolite of 6-TG formed in hgprt+ cells (6-TG sensitive) is transferred into hgprt− cells (6-TG resistant) through gap junction, so that both of the cells die. On the other hand, when the intracellular communication is inhibited by the test compound, only the hgprt− cells survive and form colonies.

As a result of the test on Compound No. 2 of the present invention and Comparative Compound I which exhibits a high systemic activity in the above Test Example 5, Compound No. 2 of the present invention was found to be negative but a significant increase of colony forming rate was observed at 7.5 and 15 µg/ml in the case of Compound I and thus Compound I was found to be positive.

Accordingly, from the test result, the compound of the present invention was found to have a lower carcinogenic risk than Compound I.

Test Example 7

Insecticidal Effect on Cat Flea

Onto a round filter (diameter: 10 cm) was added dropwise 0.7 ml of an agent solution diluted to a predetermined concentration. After drying, the filter was placed on the bottom of a cylinder (diameter: 10 cm×height: 30 cm). Ten fleas were set free therein and the mortality was investigated on 1st day and 2nd day after the treatment to calculate a death rate (%) based on the results. The results are shown in Table 7 (the compound numbers in the table correspond to the numbers in Table 1).

TABLE 7

| Compound No. | Amount of Agent Tested (mg/filter) | Death Rate (%) |
|---|---|---|
| 2 | 0.7 | 100 |

The 1-aryl-3-cyano-5-pyridylalkylaminopyrazole derivatives of the present invention are compounds useful as novel pest control agents having combined characteristics of a systemic activity and a high safety in addition to an excellent insecticidal activity and a wide insecticidal spectrum.

The present invention is precisely explained with reference to specific embodiments but it is obvious for those skilled in the art that various changes and modifications can be carried out without departing from the spirit and scope of the present invention.

The present application is based on Japanese Patent Application No. 2000-230238 filed on Jul. 31, 2000 and the entire content is incorporated herein as reference.

What is claimed is:
1. 1-(2,6-dichloro-4-trifluoromethylphenyl)-4-difluoromethylthio-5-(pyridin-2-ylmethylamino)pyrazole-3-carbonitrile.

* * * * *